United States Patent
Neira et al.

(10) Patent No.: US 8,080,542 B2
(45) Date of Patent: Dec. 20, 2011

(54) S1P RECEPTOR MODULATING COMPOUNDS AND USE THEREOF

(75) Inventors: Susana C. Neira, Thousand Oaks, CA (US); Xiang Yu, Acton, MA (US); Roland Burli, Bishop's Stortford (GB); Victor Cee, Thousand Oaks, CA (US); Brian Lanman, Oak Park, CA (US)

(73) Assignees: Amgen, Inc., Thousand Oaks, CA (US); Epix Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 12/234,514

(22) Filed: Sep. 19, 2008

(65) Prior Publication Data

US 2009/0082331 A1    Mar. 26, 2009

Related U.S. Application Data

(60) Provisional application No. 60/994,812, filed on Sep. 20, 2007.

(51) Int. Cl.
*A61K 31/397* (2006.01)
*C07D 205/04* (2006.01)

(52) U.S. Cl. .................. 514/210.17; 548/953
(58) Field of Classification Search ............... None
See application file for complete search history.

(56) References Cited

U.S. PATENT DOCUMENTS

| | | | |
|---|---|---|---|
| 3,329,781 A | 7/1967 | Wiser | |
| 4,767,896 A | 8/1988 | Nigg et al. | |
| 5,145,865 A * | 9/1992 | Fujii et al. ............... | 514/424 |
| 5,614,531 A | 3/1997 | Juraszyk et al. | |
| 5,880,284 A | 3/1999 | Himmelsbach et al. | |
| 6,384,061 B1 | 5/2002 | Lee et al. | |
| 6,411,326 B1 | 6/2002 | Tabata | |
| 6,541,203 B2 * | 4/2003 | Mitchison ............... | 435/6 |
| 2002/0156074 A1 | 10/2002 | Barvian et al. | |
| 2002/0183519 A1 | 12/2002 | Nar et al. | |
| 2005/0014725 A1 | 1/2005 | Mi et al. | |
| 2005/0113283 A1 | 5/2005 | Solow-Cordero et al. | |
| 2006/0135786 A1 | 6/2006 | Saha et al. | |
| 2006/0173043 A1 * | 8/2006 | Han et al. ............... | 514/317 |
| 2007/0173487 A1 | 7/2007 | Saha et al. | |
| 2008/0015177 A1 | 1/2008 | Saha et al. | |
| 2008/0027036 A1 * | 1/2008 | Burli et al. ............... | 514/210.18 |
| 2008/0064677 A9 | 3/2008 | Saha et al. | |
| 2009/0285772 A1 * | 11/2009 | Phiasivongsa et al. ..... | 424/85.2 |

FOREIGN PATENT DOCUMENTS

| | | |
|---|---|---|
| EP | 1 553 075 A1 | 7/2005 |
| JP | 10-204059 | 8/1998 |
| JP | 10-204059 A | 8/1998 |
| WO | WO 97/45402 * | 12/1997 |
| WO | 02064616 A2 | 8/2002 |
| WO | 03061567 A2 | 7/2003 |
| WO | 03062252 A1 | 7/2003 |
| WO | 03105771 A2 | 12/2003 |
| WO | 2004048383 A1 | 6/2004 |
| WO | 2004062663 A1 | 7/2004 |
| WO | 2004113330 A1 | 12/2004 |
| WO | 2005020882 A3 | 3/2005 |
| WO | 2006064757 A1 | 6/2006 |
| WO | 2007061458 A2 | 5/2007 |
| WO | 2007109330 A2 | 9/2007 |
| WO | 2007109334 A2 | 9/2007 |
| WO | WO 2007/109334 * | 9/2007 |
| WO | 2009038759 A2 | 3/2009 |

OTHER PUBLICATIONS

Abdel-Rahman, T.M. Mans. Sci. Bull. (A Chem), vol. 25, No. 1, Jun. 1998.*
Traynor et al., 1995, "Modulation by μ-opioid agonists of guanosine-5'-O-(3-[35S]thio)triphosphate binding to membranes from human neuroblastoma SH-SY5Y cells," Molecular Pharmacology, 47, 848-854.
Zemann et al., 2006, "Sphingosine kinase type 2 is essential for lymphopenia induced by the immunomodulatory drug FTY720," Blood, 107(4), 1454-1458.
Pan et al., 2006, "A monoselective sphingosine-1-phospate receptor-1 agonist prevents allograft rejection in a stringent rat heart transplantation model," Chemistry & Biology, 13, 1227-1234.

* cited by examiner

*Primary Examiner* — Rebecca Anderson
*Assistant Examiner* — Alicia L Otton
(74) *Attorney, Agent, or Firm* — McDonnell Boehnen Hulbert & Berghoff LLP

(57) ABSTRACT

The present invention relates to amides that have activity as SIP receptor modulating agents and the use of such compounds to treat diseases associated with inappropriate S1P receptor activity. The compounds may be used as immunomodulators, e.g., for treating or preventing diseases such as autoimmune and related immune disorders including systemic lupus erythematosus, inflammatory bowel diseases such as Crohn's disease and ulcerative colitis, type I diabetes, uveitis, psoriasis, myasthenia gravis, rheumatoid arthritis, non-glomerular nephrosis, hepatitis, Behçet's disease, glomerulonephritis, chronic thrombocytopenic purpura, hemolytic anemia, hepatitis and Wegner's granuloma; and for treating other conditions.

8 Claims, No Drawings

S1P RECEPTOR MODULATING COMPOUNDS AND USE THEREOF

This application claims the benefit of U.S. provisional No. 60/994,812, filed Sep. 20, 2007, the content of which is incorporated herein by reference in its entirety.

FIELD OF THE INVENTION

The present invention relates to compounds that have activity as S1P receptor modulating agents and the use of such compounds to treat diseases associated with inappropriate SIP receptor activity.

BACKGROUND OF THE INVENTION

Sphingosine-1-phosphate (S1P) has been demonstrated to induce many cellular effects, including those that result in platelet aggregation, cell proliferation, cell morphology, tumor cell invasion, endothelial cell chemotaxis and endothelial cell in vitro angiogenesis. S1P receptors are therefore good targets for therapeutic applications such as wound healing and tumor growth inhibition. S1P signals cells in part via a set of G protein-coupled receptors named S1P1, S1P2, S1P3, S1P4, and S1P5 (formerly called EDG-1, EDG-5, EDG-3, EDG-6, and EDG-8, respectively). These receptors share 50-55% amino acid and cluster identity with three other receptors (LPA1, LPA2, and LPA3 (formerly EDG-2, EDG-4 and EDG-7)) for the structurally-related lysophosphatidic acid (LPA).

A conformational shift is induced in the G-Protein Coupled Receptor (GPCR) when the ligand binds to that receptor, causing GDP to be replaced by GTP on the α-subunit of the associated G-proteins and subsequent release of the G-proteins into the cytoplasm. The α-subunit then dissociates from the βγ-subunit, and each subunit can then associate with effector proteins, which activate second messengers leading to a cellular response. Eventually the GTP on the G-proteins is hydrolyzed to GDP, and the subunits of the G-proteins re-associate with each other and then with the receptor. Amplification plays a major role in the general GPCR pathway. The binding of one ligand to one receptor leads to the activation of many G-proteins, each capable of associating with many effector proteins, leading to an amplified cellular response.

S1P receptors make good drug targets, because individual receptors are both tissue- and response-specific. Tissue specificity of the S1P receptors is important, because development of an agonist or antagonist selective for one receptor localizes the cellular response to tissues containing that receptor, limiting unwanted side effects. Response specificity of the S1P receptors is also important because it allows for development of agonists or antagonists that initiate or suppress certain cellular responses without affecting other things. For example, the response specificity of the S1P receptors could allow for an S1P mimetic that initiates platelet aggregation without affecting cell morphology.

S1P is formed as a metabolite of sphingosine in its reaction with sphingosine kinase, and is abundantly stored in platelet aggregates where high levels of sphingosine kinase exist and sphingosine lyase is lacking. S1P is released during platelet aggregation, accumulates in serum and is also found in malignant ascites. S1P biodegradation most likely proceeds via hydrolysis by ectophosphohydrolases, specifically the sphingosine 1-phosphate phosphohydrolases.

SUMMARY OF THE INVENTION

The present invention relates to the use of new compositions which include S1P modulators, e.g., agonists, partial agonists, inverse agonists and antagonists, and their use in treating, preventing or curing various S1P receptor-related conditions. The invention features compounds which are S1P receptor modulators; in an embodiment, such compounds include those having the formula

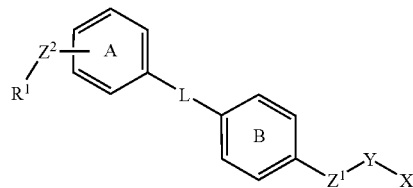

and pharmaceutically acceptable salts thereof, wherein $R^1$, $Z^2$, L, B, A, $Z^1$, $Z^2$, Y and X are defined herein.

DETAILED DESCRIPTION OF THE INVENTION

In one embodiment, the present invention relates to a compound having the formula

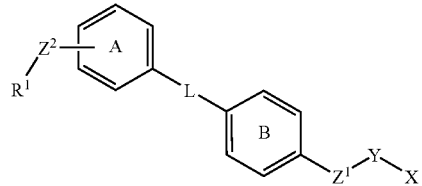

or a pharmaceutically-acceptable salt thereof, wherein:

A is phenyl or a six-membered heteroaryl containing 1 or 2 N atoms, the phenyl and heteroaryl being substituted by 0, 1, 2 or 3 substituents selected from F, Cl, Br, $OC_{1-4}$alk, $C_{1-4}$alk, and $C_{1-4}$haloalk;

B is phenyl or a six-membered heteroaryl containing 1 or 2 N atoms, the phenyl and heteroaryl being substituted by 0, 1, 2 or 3 substituents selected from F, Cl, Br, $OC_{1-4}$alk, $C_{1-4}$alk, and $C_{1-4}$haloalk;

L is —C≡C—, —$CH_2CH_2$—, —$N(R^a)C(=O)$— or —$C(=O)N(R^a)$—;

n is 0, 1, 2 or 3;

$R^a$ is, independently in each instance; H or $C_{1-6}$alk;

$R^1$ is selected from $C_{1-6}$alk, $OC_{1-5}$alk, $N(Ra)C_{1-5}$alk, $N(C_{1-5}alk)C_{1-5}$alk, aryl or heteroaryl.

X is selected from $WC(=O)OR^{6a}$, $WP(=O)R^{6b}R^{6c}$, $WS(=O)_2OH$, $WCONHSO_3H$ or 1H-tetrazol-5-yl; wherein W is a direct bond, oxygen or $C_{1-4}$alk having one or more substituents independently selected from halogen, OH, cyano, $NR^aR^a$, arylamino, heteroarylamino, $OC_{1-4}$alk and $CO_2H$; $R^{6a}$ is hydrogen or $C_{1-4}$alk; and $R^{6b}$ and $R^{6c}$ are independently hydrogen, OH, $C_{1-4}$alk or $C_{1-4}$haloalk;

Y is residue of formula (a) wherein the left and right asterisks indicate the point of attachment

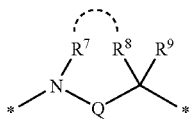

(a)

wherein

Q is selected from a direct bond, C=O, C=S, SO$_2$, C=ONR$^a$ or (CR$^{10}$OR$^{11}$)$_m$; and m is 0, 1, 2 or 3;

R$^7$ and R$^8$ are independently selected from hydrogen, halogen, amino, C$_{1-5}$alkamino, OH, cyano, C$_{1-6}$alk, C$_{1-6}$alk(OH), SC$_{1-5}$alk, OC$_{1-5}$alk, C$_{1-6}$haloalk and OC$_{1-5}$alk; or R$^7$ and R$^8$ may be joined together with the atoms to which they are attached to form a 4- to 7-membered ring, optionally having a heteroatom selected from N, O and S; and R$^9$ is selected from hydrogen, halogen, OH, cyano, C$_{1-6}$alk, SC$_{1-5}$alk, OC$_{1-5}$alk, C$_{1-6}$haloalk or OC$_{1-5}$haloalk;

R$^{10}$ and R$^{11}$ are independently selected from hydrogen, halogen, OH, cyano, C$_{1-6}$alk, OC$_{1-5}$alk, SC$_{1-5}$alk, C$_{1-6}$-haloalk or OC$_{1-5}$haloalk and Z$^1$ and Z$^2$ are independently selected from O, NR$^3$, S, S(=O), S(=O)$_2$, S(=O)$_2$NR$^3$, (CR$^4$R$^5$)$_n$, C=O, C=S, C=N—R$^3$, or a direct bond, wherein R$^3$ is selected from hydrogen, OH, SO$_2$, C=O, C=S, C=NH, C$_{1-6}$-alk, OC$_{1-5}$alk, SC$_{1-5}$alk, C$_{1-6}$haloalk and OC$_{1-5}$haloalk, aryl or heteroaryl; or when Z$^2$ is a direct bond, R$_3$ is a C$_3$-C$_6$ ring optionally containing a heteroatom; and R$^4$ and R$^5$ are independently selected from hydrogen, halogen, OH, cyano, C$_{1-6}$alk, OC$_{1-5}$alk, SC$_{1-5}$alk, C$_{1-6}$haloalk and OC$_{1-5}$haloalk, aryl and heteroaryl or together form C=O.

In another embodiment, in conjunction with any above or below embodiments, A is phenyl additionally substituted by 0, 1, 2 or 3 substituents selected from F, Cl, Br, OC$_{1-4}$alk, C$_{1-4}$alk, and C$_{1-4}$haloalk.

In another embodiment, in conjunction with any above or below embodiments, A is 1,4-phenyl additionally substituted by 0, 1, 2 or 3 substituents selected from F, Cl, Br, OC$_{1-4}$alk, C$_{1-4}$alk, and C$_{1-4}$haloalk.

In another embodiment, in conjunction with any above or below embodiments, A is 1,3-phenyl additionally substituted by 0, 1, 2 or 3 substituents selected from F, Cl, Br, OC$_{1-4}$alk, C$_{1-4}$alk, and C$_{1-4}$haloalk.

In another embodiment, in conjunction with any above or below embodiments, A is 1,2-phenyl additionally substituted by 0, 1, 2 or 3 substituents selected from F, Cl, Br, OC$_{1-4}$alk, C$_{1-4}$alk, and C$_{1-4}$haloalk.

In another embodiment, in conjunction with any above or below embodiments, A is pyrdinyl additionally substituted by 0, 1, 2 or 3 substituents selected from F, Cl, Br, OC$_{1-4}$alk, C$_{1-4}$alk, and C$_{1-4}$haloalk.

In another embodiment, in conjunction with any above or below embodiments, A is pyrimidinyl additionally substituted by 0, 1, 2 or 3 substituents selected from F, Cl, Br, OC$_{1-4}$alk, C$_{1-4}$alk, and C$_{1-4}$haloalk.

In another embodiment, in conjunction with any above or below embodiments, B is phenyl additionally substituted by 0, 1, 2 or 3 substituents selected from F, Cl, Br, OC$_{1-4}$alk, C$_{1-4}$alk, and C$_{1-4}$haloalk.

In another embodiment, in conjunction with any above or below embodiments, B is pyrdinyl additionally substituted by 0, 1, 2 or 3 substituents selected from F, Cl, Br, OC$_{1-4}$alk, C$_{1-4}$alk, and C$_{1-4}$haloalk.

In another embodiment, in conjunction with any above or below embodiments, B is pyrimidinyl additionally substituted by 0, 1, 2 or 3 substituents selected from F, Cl, Br, OC$_{1-4}$alk, C$_{1-4}$alk, and C$_{1-4}$haloalk.

In another embodiment, in conjunction with any above or below embodiments, A is phenyl additionally substituted by 0, 1, 2 or 3 substituents selected from F, Cl, Br, OC$_{1-4}$alk, C$_{1-4}$alk, and C$_{1-4}$haloalk; and B is phenyl additionally substituted by 0, 1, 2 or 3 substituents selected from F, Cl, Br, OC$_{1-4}$alk, C$_{1-4}$alk, and C$_{1-4}$haloalk.

In another embodiment, in conjunction with any above or below embodiments, L is —N(R$^a$)C(=O)—.

In another embodiment, in conjunction with any above or below embodiments, L is —C(=O)N(R$^a$)—.

In another embodiment, in conjunction with any above or below embodiments, L is —C≡C—.

In another embodiment, in conjunction with any above or below embodiments, L is —CH$_2$CH$_2$—.

In another embodiment, in conjunction with any above or below embodiments, —Y—X is

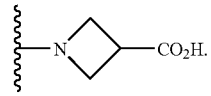

Another aspect of the invention relates to a compound having the formula

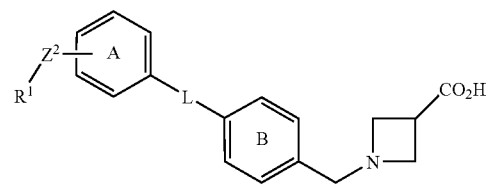

or a pharmaceutically-acceptable salt thereof, wherein:

A is phenyl or a six-membered heteroaryl containing 1 or 2 N atoms, the phenyl and heteroaryl being substituted by 0, 1, 2 or 3 substituents selected from F, Cl, Br, C$_{1-4}$alk, and C$_{1-4}$haloalk;

B is phenyl or a six-membered heteroaryl containing 1 or 2 N atoms, the phenyl and heteroaryl being substituted by 0, 1, 2 or 3 substituents selected from F, Cl, Br, C$_{1-4}$alk, and C$_{1-4}$haloalk;

L is —N(R$^a$)C(=O)— or —C(=O)N(R$^a$)—;

n is 0, 1, 2 or 3;

R$^a$ is, independently in each instance; H or C$_{1-6}$alk;

R$^1$ is selected from C$_{1-6}$alk, OC$_{1-5}$alk, N(Ra)C$_{1-5}$alk, N(C$_{1-5}$alk)C$_{1-5}$alk, aryl or heteroaryl.

Z$^1$ is selected from O, NR$^3$, S, S(=O), S(=O)$_2$, S(=O)$_2$NR$^3$, (CR$^4$R$^5$)$_n$, C=O, C=S, C=N—R$^3$, or a direct bond, wherein R$^3$ is selected from hydrogen, OH, SO$_2$, C=O, C=S, C=NH, C$_{1-6}$alk, OC$_{1-5}$alk, SC$_{1-5}$alk, C$_{1-6}$haloalk and OC$_{1-5}$haloalk, aryl or heteroaryl; or when Z$^2$ is a direct bond, R$_3$ is a C$_3$-C$_6$ ring optionally containing a heteroatom; and R$^4$ and R$^5$ are independently selected from hydrogen, halogen, OH, cyano, C$_{1-6}$alk, OC$_{1-5}$alk, SC$_{1-5}$alk, C$_{1-6}$haloalk and OC$_{1-5}$haloalk, aryl and heteroaryl or together form C=O.

In another embodiment of the invention, in conjunction with the above and below embodiments, R$^1$ is selected from phenyl and heteroaryl; both of which are optionally substituted with halogen.

In another embodiment of the invention, in conjunction with the above and below embodiments, $R^1$ is phenyl optionally substituted with halogen.

In another embodiment of the invention, in conjunction with the above and below embodiments, $R^1$ is heteroaryl optionally substituted with halogen.

In another embodiment of the invention, in conjunction with the above and below embodiments, $R^1$ is phenyl.

In another embodiment of the invention, in conjunction with the above and below embodiments, $R^1$ is heteroaryl.

In another embodiment of the invention, in conjunction with the above and below embodiments, $R^1$ is 5- or 6-membered unsaturated ring including one atom selected from N, O and S, and 0, 1, 2 or 3 additional N atoms.

In another embodiment of the invention, in conjunction with the above and below embodiments, $R^1$ is selected from pyridinyl, pyrimidine, thiazolyl, oxazolyl, furanyl and thiophenyl.

In another embodiment of the invention, in conjunction with the above and below embodiments, X is $WC(O)OR^{6a}$, $WP(O)R^{6b}R^{6c}$, $WS(O)_2OH$, $WCONHSO_3H$ or 1H-tetrazol-5-yl. W is a direct bond, oxygen or $C_{1-4}$ alkyl with substituents independently selected from halogen, hydroxyl, cyano, amino, alkylamino, arylamino, heteroarylamino and $C_{1-4}$ alkoxy; and $R^{6a}$ is hydrogen or $C_{1-4}$ alkyl; $R^{6b}$ and $R^{6c}$ are independently selected from hydrogen, hydroxyl, $C_{1-4}$ alkyl and halogen substituted $C_{1-4}$ alkyl.

In another embodiment of the invention, in conjunction with the above and below embodiments, X is $CO_2H$.

In another embodiment of the invention, in conjunction with the above and below embodiments, Y is

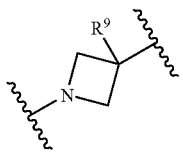

wherein $R^9$ is selected from hydrogen, halogen, hydroxyl, cyano, $C_{1-6}$ alkyl, $C_{1-5}$ alkylthio, $C_{1-5}$ alkoxy, halogen-substituted $C_{1-6}$ alkyl and halogen-substituted $C_{1-5}$ alkoxy.

In another embodiment of the invention, in conjunction with the above and below embodiments, Y is

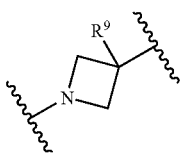

wherein $R^9$ is selected from hydrogen, halogen and hydroxyl.

In another embodiment of the invention, in conjunction with the above and below embodiments, $R^9$ is hydrogen.

In another embodiment of the invention, in conjunction with the above and below embodiments, $R^9$ is hydroxyl.

In another embodiment of the invention, in conjunction with the above and below embodiments, $Z^1$ is $CR^4R^5$; wherein $R^4$ and $R^5$ are independently hydrogen, halogen, hydroxyl, cyano, $C_{1-6}$ alkyl, $C_{1-5}$ alkoxy, $C_{1-5}$ alkylthio, halogen-substituted $C_{1-6}$ alkyl or halogen-substituted $C_{1-5}$ alkoxy.

In another embodiment of the invention, in conjunction with the above and below embodiments, $Z^1$ is $CR^4R^5$; wherein $R^4$ and $R^5$ are independently hydrogen, halogen, $C_{1-6}$ alkyl or halogen-substituted $C_{1-6}$ alkyl.

In another embodiment of the invention, in conjunction with the above and below embodiments, $Z^1$ is $CH_2$.

In another embodiment of the invention, in conjunction with the above and below embodiments, $Z^2$ is selected from O, $NR^3$, S, S(O), $S(O)_2$, $S(O)_2NR^3$, $(CR^4R^5)_n$, C=O, C=S, and C=N—$R^3$;

$R^3$ is hydrogen, hydroxyl, $C_{1-6}$ alkyl, $C_{1-5}$ alkoxy, $C_{1-5}$ alkylthio, halogen-substituted $C_{1-6}$ alkyl or halogen-substituted $C_{1-5}$ alkoxy;

$R^4$ and $R^5$ are independently selected from hydrogen, halogen, hydroxyl, cyano, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy, or together form "C=O"; and n is 1, 2 or 3.

In another embodiment of the invention, in conjunction with the above and below embodiments, $Z^2$ is selected from O, $NR^3$, S, S(O), $S(O)_2$, $S(O)_2NR^3$, $CR^4R^5$, C=O, C=S, and C=N—$R^3$;

$R^3$ is hydrogen, hydroxyl, $C_{1-6}$ alkyl, $C_{1-5}$ alkoxy, $C_{1-5}$ alkylthio, halogen-substituted $C_{1-6}$ alkyl or halogen-substituted $C_{1-5}$ alkoxy; and $R^4$ and $R^5$ are independently selected from hydrogen, halogen, hydroxyl, cyano, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy.

In another embodiment of the invention, in conjunction with the above and below embodiments $Z^2$ is selected from O, $NR^3$, S, $CR^4R^5$, C=O, C=S, and C=N—$R^3$;

$R^3$ is hydrogen, hydroxyl, $C_{1-6}$ alkyl, $C_{1-5}$ alkoxy, $C_{1-5}$ alkylthio, halogen-substituted $C_{1-6}$ alkyl or halogen-substituted $C_{1-5}$ alkoxy; and $R^4$ and $R^5$ are independently selected from hydrogen, halogen, hydroxyl, cyano, $C_{1-6}$ alkyl, $C_{1-5}$ alkoxy, $C_{1-5}$ alkylthio, halogen-substituted $C_{1-6}$ alkyl and halogen-substituted $C_{1-5}$ alkoxy.

In another embodiment of the invention, in conjunction with the above and below embodiments $Z^2$ is selected from O, S, $CH_2$, C=O, C=S and C=N—OH.

The specification and claims contain listing of species using the language "selected from . . . and . . . " and "is . . . or . . ." (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

In one aspect, the present invention provides methods for modulating S1P-1 receptor mediated biological activity. The present invention also provides methods for using S1P-1 modulators (i.e., agonists or antagonists) in treating or preventing diseases such as ovarian cancer, peritoneal cancer, endometrial cancer, cervical cancer, breast cancer, colorectal cancer, uterine cancer, stomach cancer, small intestine cancer, thyroid cancer, lung cancer, kidney cancer, pancreas cancer and prostrate cancer; acute lung diseases, adult respiratory distress syndrome ("ARDS"), acute inflammatory exacerbation of chronic lung diseases such as asthma, surface epithelial cell injury such as transcorneal freezing or cutaneous burns, and cardiovascular diseases such as ischemia in a subject in need of such treatment or prevention.

In another aspect, the invention provides methods for using S1P-1 modulators in treating or preventing disorders such as, but not limited to, vasoconstriction in cerebral arteries, autoimmune and related immune disorders including systemic lupus erythematosus, inflammatory bowel diseases such as Crohn's disease and ulcerative colitis, type I diabetes, uveitis, psoriasis, myasthenia gravis, rheumatoid arthritis, non-glomerular nephrosis, hepatitis, Behçet's disease, glomerulonephritis, chronic thrombocytopenic purpura, hemolytic anemia, hepatitis and Wegner's granuloma.

In still another aspect, the invention provides methods for using S1P-1 modulators to treat or prevent a disease or disorder in a subject, comprising administering to a subject in need of such treatment or prevention a therapeutically effective amount of an S1P-1 modulator, e.g., an agonist, that stimulates the immune system. In certain embodiments, the subject is afflicted by an infectious agent. In other embodiments, the subject is immunocompromised.

In still another aspect, the present invention provides a method of modulating an S1P-1 receptor-mediated biological activity in a cell. A cell expressing the S1P-1 receptor is contacted with an amount of an S1P-1 receptor modulator sufficient to modulate the S1P-1 receptor mediated biological activity.

In yet another aspect, the present invention provides a method for modulating an S1P-1 receptor mediated biological activity in a subject. In such a method, an amount of a modulator of the S1P-1 receptor effective to modulate an S1P-1 receptor-mediated biological activity is administered to the subject.

In yet another aspect, the present invention provides a method for treating, preventing or ameliorating an S1P-1 receptor mediated condition in a subject. In such a method, an amount of a modulator of the S1P-1 receptor effective to modulate an S1P-1 receptor-mediated biological activity is administered to the subject. The S1P-1 receptor mediated condition may be, e.g., transplant rejection (solid organ transplant and islet cells); transplant rejection (tissue); cancer; autoimmune/inflammatory diseases; rheumatoid arthritis; lupus; insulin dependent diabetes (Type I); non-insulin dependent diabetes (Type II); multiple sclerosis; psoriasis; ulcerative colitis; inflammatory bowel disease; Crohn's disease; acute and chronic lymphocytic leukemias and lymphomas.

The features and other details of the invention will now be more particularly described. It will be understood that particular embodiments described herein are shown by way of illustration and not as limitations of the invention. The principal features of this invention can be employed in various embodiments without departing from the scope of the invention. All parts and percentages are by weight unless otherwise specified.

DEFINITIONS

For convenience, certain terms used in the specification and examples are collected here.

"Treating", includes any effect, e.g., lessening, reducing, modulating, or eliminating, that results in the improvement of the condition, disease, disorder, etc.

"$C_{\alpha-\beta}$alk" means an alkyl group comprising a minimum of $\alpha$ and a maximum of $\beta$ carbon atoms in a branched, cyclical or linear relationship or any combination of the three, wherein $\alpha$ and $\beta$ represent integers. The alkyl groups described in this section may also contain one or two double or triple bonds. A designation of $C_0$alk indicates a direct bond. Examples of $C_{1-6}$alkyl include, but are not limited to, the following:

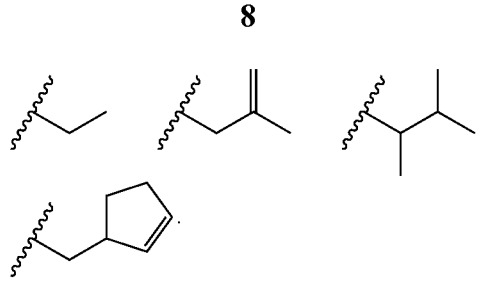

"Halo" or "halogen" means a halogen atoms selected from F, Cl, Br and I.

"$C_{V-W}$haloalk" means an alk group, as described above, wherein any number—at least one—of the hydrogen atoms attached to the alk chain are replaced by F, Cl, Br or I.

"Substituted alkyls" refers to alkyl moieties having substituents replacing a hydrogen on one or more carbons of the hydrocarbon backbone. Such substituents can include alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino, acylamino, amidino, imino, sulfhydryl, alkylthio, thiocarboxylate, sulfates, alkylsulfinyl, sulfonato, sulfamoyl, sulfonamido, nitro, trifluoromethyl, cyano, azido, or heterocyclyl.

"Aryl" includes groups with aromaticity, including 5- and 6-membered unconjugated (i.e., single-ring) aromatic groups that may include from zero to four heteroatoms, as well as conjugated (i.e., multicyclic) systems having at least one ring that is aromatic. Examples of aryl groups include benzene, phenyl, tolyl and the like. Multicyclic aryl groups include tricyclic and bicyclic systems, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, indolizine, tetralin, and methylenedioxyphenyl.

Aryl groups having heteroatoms in the ring structure may also be referred to as "aryl heterocycles", "heterocycles," "heteroaryls" or "heteroaromatics"; e.g., pyrrole, furan, thiophene, thiazole, isothiazole, imidazole, triazole, tetrazole, pyrazole, oxazole, isooxazole, pyridine, pyrazine, pyridazine, and pyrimidine. The aromatic ring can be substituted at one or more ring positions with, for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino, acylamino, amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "alkylaryl" or an "aralkyl" moiety is an alkyl substituted with an aryl group (e.g., phenylmethyl(benzyl)).

Unless the number of carbons is otherwise specified, "lower alkyl" includes an alk group, as defined above, but having from one to ten, more preferably from one to six, carbon atoms in its backbone structure. "Lower alkenyl" and "lower alkynyl" have chain lengths of, for example, 2-5 carbon atoms.

"Acyl" includes compounds and moieties which contain the acyl radical (CH$_3$CO—) or a carbonyl group. "Substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Acylamino" includes moieties wherein an acyl moiety is bonded to an amino group. For example, the term includes alkylcarbonylamino, arylcarbonylamino, carbamoyl and ureido groups. "Alkylamino" includes moieties wherein an alkyl moiety is bonded to an amino group; "dialkylamino", "arylamino", "diarylamino", and "alkylarylamino" are analogously named. In some embodiments, "amino" may include acylamino and/or alkylamino groups.

"Alkoxyalkyl", "alkylaminoalkyl" and "thioalkoxyalkyl" include alkyl groups, as described above, which further include oxygen, nitrogen or sulfur atoms replacing one or more hydrocarbon backbone carbon atoms, e.g., oxygen, nitrogen or sulfur atoms.

"Alkoxy" includes alkyl, alkenyl, and alkynyl groups covalently linked to an oxygen atom. Examples of alkoxy groups include methoxy, ethoxy, isopropyloxy, propoxy, butoxy, and pentoxy groups. Examples of "substituted alkoxy" groups include halogenated alkoxy groups. Substituted alkoxy groups can include alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, or heterocyclyl substituents. Examples of halogen-substituted alkoxy groups include fluoromethoxy, difluoromethoxy, trifluoromethoxy, chloromethoxy, dichloromethoxy, and trichloromethoxy.

The terms "heterocyclyl" or "heterocyclic group" include closed ring structures, e.g., 3- to 10-, or 4- to 7-membered rings which include one or more heteroatoms. Heterocyclyl groups can be saturated or unsaturated and include pyrrolidine, oxolane, thiolane, piperidine, piperizine, morpholine, lactones, lactams such as azetidinones and pyrrolidinones, sultams, sultones, and the like.

Heterocyclic rings may be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino, acylamino, amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or heteroatoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O$^-$.

The term "halogen" includes fluorine, bromine, chlorine, iodine, etc. The term "perhalogenated" generally refers to a moiety wherein all hydrogens are replaced by halogen atoms.

"Heteroatom" includes atoms of any element other than carbon or hydrogen. Examples of heteroatoms include nitrogen, oxygen, sulfur and phosphorus.

"At least partially aromatic bicyclic ring system", means a bicyclic ring system where either or both of the rings forming the bicycle are aromatic.

It will be noted that the structure of some of the compounds of the invention includes asymmetric carbon atoms. It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

"Combination therapy" (or "co-therapy") includes the administration of a S1P receptor modulator of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients and non-drug therapies (e.g. surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

An "anionic group," as used herein, refers to a group that is negatively charged at physiological pH. Preferred anionic groups include carboxylate, sulfate, sulfonate, sulfinate, sulfamate, tetrazolyl, phosphate, phosphonate, phosphinate, or phosphorothioate or functional equivalents thereof. "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. *The Organic Chemistry of Drug Design and Drug Action*, Academic Press, Inc.: San Diego, Calif., 1992, pp. 19-23). A particularly preferred anionic group is a carboxylate.

The term "heterocyclic group" is intended to include closed ring structures in which one or more of the atoms in the ring is an element other than carbon, for example, nitrogen, or oxygen or sulfur. Heterocyclic groups can be saturated or unsaturated and heterocyclic groups such as pyrrole and furan can have aromatic character. They include fused ring structures such as quinoline and isoquinoline. Other examples of heterocyclic groups include pyridine and purine. Heterocyclic groups can also be substituted at one or more constituent atoms with, for example, a halogen, a lower alkyl, a lower alkenyl, a lower alkoxy, a lower alkylthio, a lower alkylamino, a lower alkylcarboxyl, a nitro, a hydroxyl, —$CF_3$, —CN, or the like.

An "S1P-modulating agent" includes compound or compositions capable of inducing a detectable change in S1P receptor activity in vivo or in vitro, e.g., at least 10% increase or decrease in S1P activity as measured by a given assay such as the bioassay described hereinbelow.

"$EC_{50}$ of an agent" included that concentration of an agent at which a given activity, including binding of sphingosine or other ligand of an S1P receptor and/or a functional activity of a S1P receptor (e.g., a signaling activity), is 50% maximal for that S1P receptor. Stated differently, the $EC_{50}$ is the concentration of agent that gives 50% activation, when 100% activation is set at the amount of activity of the S1P receptor which does not increase with the addition of more ligand/agonist and 0% activation is set at the amount of activity in the assay in the absence of added ligand/agonist.

"Purified" and like terms relate to the isolation of a molecule or compound in a form that is substantially free of contaminants normally associated with the molecule or compound in a native or natural environment.

An "effective amount" includes an amount sufficient to produce a selected effect. For example, an effective amount of an S1P receptor antagonist is an amount that decreases the cell signaling activity of the S1P receptor.

"Immunomodulation" includes effects on the functioning of the immune system, and includes both the enhancement of an immune response as well as suppression of the immune response.

The compounds of the invention and the other pharmacologically active agent may be administered to a patient simultaneously, sequentially or in combination. It will be appreciated that when using a combination of the invention, the compound of the invention and the other pharmacologically active agent may be in the same pharmaceutically acceptable carrier and therefore administered simultaneously. They may be in separate pharmaceutical carriers such as conventional oral dosage forms which are taken simultaneously. The term "combination" further refers to the case where the compounds are provided in separate dosage forms and are administered sequentially.

The compounds of the invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

An appropriate dosage level will generally be about 0.001 to 50 mg per kg patient body weight per day, which may be administered in single or multiple doses. Preferably, the dosage level will be about 0.01 to about 25 mg/kg per day; more preferably about 0.05 to about 10 mg/kg per day. For example, in the treatment or prevention of a disorder of the central nervous system, a suitable dosage level is about 0.001 to 10 mg/kg per day, preferably about 0.005 to 5 mg/kg per day, and especially about 0.01 to 1 mg/kg per day. The compounds may be administered on a regimen of 1 to 4 times per day, preferably once or twice per day.

It will be appreciated that the amount of the compound of the invention required for use in any treatment will vary not only with the particular compounds or composition selected but also with the route of administration, the nature of the condition being treated, and the age and condition of the patient, and will ultimately be at the discretion of the attendant physician.

The compositions and combination therapies of the invention may be administered in combination with a variety of pharmaceutical excipients, including stabilizing agents, carriers and/or encapsulation formulations as described herein.

Aqueous compositions of the present invention comprise an effective amount of the compounds of the invention, dissolved or dispersed in a pharmaceutically acceptable carrier or aqueous medium.

"Pharmaceutically or pharmacologically acceptable" include molecular entities and compositions that do not produce an adverse, allergic or other untoward reaction when administered to an animal, or a human, as appropriate. "Pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For human administration, preparations should meet sterility, pyrogenicity, general safety and purity standards as required by FDA Office of Biologics standards.

The compositions and combination therapies of the invention will then generally be formulated for parenteral administration, e.g. formulated for injection via the intravenous, intramuscular, subcutaneous, intralesional, or even intraperitoneal routes. The preparation of an aqueous composition that contains a composition of the invention or an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Therapeutic or pharmacological compositions of the present invention will generally comprise an effective amount of the component(s) of the combination therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including cremes, lotions, mouthwashes, inhalants and the like.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for intramuscular injection is also contemplated. In this regard, the use of DMSO as solvent is preferred as this will result in extremely rapid penetration, delivering high concentrations of the active compound(s) or agent(s) to a small area.

The use of sterile formulations, such as saline-based washes, by surgeons, physicians or health care workers to cleanse a particular area in the operating field may also be particularly useful. Therapeutic formulations in accordance with the present invention may also be reconstituted in the form of mouthwashes, or in conjunction with antifungal reagents. Inhalant forms are also envisioned. The therapeutic formulations of the invention may also be prepared in forms suitable for topical administration, such as in cremes and lotions.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. One dosage could be dissolved in 1 mL of isotonic NaCl solution and either added to 1000 mL of hypodermolysis fluid or injected at the proposed site of infusion, (see for example, *Remington's Pharmaceutical Sciences* 15th Edition, pages 1035-1038 and 1570-1580).

In certain embodiments, active compounds may be administered orally. This is contemplated for agents which are generally resistant, or have been rendered resistant, to proteolysis by digestive enzymes. Such compounds are contemplated to include chemically designed or modified agents; dextrorotatory peptides; and peptide and liposomal formulations in time release capsules to avoid peptidase and lipase degradation.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze drying techniques which yield a powder of the active ingredient plus any additional desired ingredient from a previously sterile-filtered solution thereof.

The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

In addition to the compounds formulated for parenteral administration, such as intravenous or intramuscular injection, other pharmaceutically acceptable forms include, e.g., tablets or other solids for oral administration; liposomal formulations; time-release capsules; and any other form currently used, including cremes.

Additional formulations suitable for other modes of administration include suppositories. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders.

In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

The pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1% to about 500 mg of the active ingredient of the invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the invention may be incorporated for administration orally or by injection include aqueous solution, suitably flavored syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For treating clinical conditions and diseases noted above, the compound of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The compounds of the present invention are high affinity agonists (or antagonists) at various S1P receptors. The compounds of the invention are also expected to evoke lymphopenia when introduced into rodents, non human primate or humans. Thus the compounds of the invention can be used as immune modulators, and are useful in treating or preventing pathologies mediated by lymphocyte actions, including acute or chronic rejection of tissue grafts such as organ transplants, and autoimmune diseases. Autoimmune diseases that may be treated with compounds of the invention include: systemic lupus erythematosus, multiple sclerosis, Behçet's disease, glomerulonephritis, rheumatoid arthritis, inflammatory bowel diseases such as Crohn's disease and ulcerative colitis, type I diabetes, uveitis, psoriasis, myasthenia gravis, Hashimoto's thyroiditis, autoimmune hemolytic anemia, autoimmune thrombocytopenic purpura, hepatitis and Wegner's granuloma.

The compounds of the invention are useful also in treating inflammatory disorders, including atopic asthma, inflammatory glomerular injury and ischemia-reperfusion injury.

Lysophospholipids, S1P and lysophosphatidic acid (LPA), stimulate cellular proliferation and affect numerous cellular functions by signaling through G protein-coupled endothelial differentiation gene-encoded (S1P) receptors. Accordingly, the S1P receptor modulators of the invention are anticipated to have utility in immunomodulation, e.g., in anti-angiogenesis therapy, such as in neoplastic disease treatment.

In one embodiment of the invention, a pharmaceutical composition comprising one or more of the S1P receptor agonists of the present invention is administered to a mammalian species, including humans, to enhance wound repair, improve neuronal function or enhance an immune response of that species. It has also been reported that S1P inhibits fibrosis in various organs. Accordingly, the S1P receptor agonists of the invention can be used to prevent/treat diseases associated with organ fibrosis, such as pulmonary fibrosis, interstitial pneumonia, chronic hepatitis, hepatic cirrhosis, chronic renal insufficiency or kidney glomerular sclerosis. In one embodiment, a composition comprising an S1P receptor agonist of the present invention is used to treat wounds, including burns, cuts, lacerations, surgical incisions, bed sores, and slow-healing ulcers such as those seen in diabetics.

In addition, S1P modulating compounds of the invention are believed to mobilize lymphocytes and increase their homing to secondary lymphoid tissues. Thus the present compounds can be used to direct lymphocytes away from transplanted organs, e.g., allografts, or healthy cells, e.g., pancreatic islets as in type I diabetes, myelin sheathing (multiple sclerosis), or other tissues that may be subjected to an undesirable immunoresponse, and thus decrease damage to such tissues from the immune system.

In another embodiment, the S1P receptor-modulating compounds of the invention are administered to a subject to treat or prevent a disorder of abnormal cell growth and differentiation. These disorders include Alzheimer's disease, aberrant corpus luteum formation, osteoporosis, anovulation, Parkinson's disease, and cancer. In one embodiment, an S1P antagonist is administered to a patient to treat a disease associated with abnormal growth.

In one embodiment, the compounds of the invention are used as immunomodulators to alter immune system activities and prevent damage to healthy tissue that would otherwise occur in autoimmune diseases and in organ transplantation. In particular, the compounds can be administered to patients as part of the treatment associated with organ transplantation, including pancreas, pancreatic islets, kidney, heart and lung transplantations. The S1P modulators can be administered alone or in combination with known immunosuppressants such as cyclosporine, tacrolimus, rapamycin, azathioprine, cyclophosphamide, methotrexate and corticosteroids such as cortisone, des-oxymetasone, betametasone, desametasone, flunisolide, prednisolone, prednisone, amcinomide, desonide, methylprednisolone, triamcinolone, and alclometasone.

S1P also acts as a survival factor in many cell types. In particular, compounds of the invention having S1P antagonistic activity are anticipated to be useful in protecting cells and tissues from hypoxic conditions. In accordance with one embodiment, compounds of the invention are administered to a patient judged to be or actually in need of treatment, to treat cells and tissues exposed to hypoxic conditions, including injury sustained as a result of ischemia. In accordance with one embodiment, compounds of the invention that show S1P receptor antagonist activity can be used to treat ischemia reperfusion type injury. Interference with the supply of oxygenated blood to tissues is defined as ischemia. The effects of ischemia are known to be progressive, so that over time cellular vitality continues to deteriorate and tissues become necrotic. Total persistent ischemia, with limited oxygen perfusion of tissues, results in cell death and eventually in coagulation-induced necrosis despite reperfusion with arterial blood. Evidence indicates that a significant proportion of the injury associated with ischemia is a consequence of the events associated with reperfusion of ischemic tissues, hence the term reperfusion injury.

Pharmaceutical compositions comprising the compounds of the invention may be administered to an individual in need by any number of routes, including topical, oral, intravenous, intramuscular, intra-arterial, intramedullary, intrathecal, intraventricular, transdermal, subcutaneous, intraperitoneal, intranasal, enteral, topical, sublingual, or rectal means. The oral route is typically employed for most conditions requiring the compounds of the invention. Preference is given to intravenous injection or infusion for the acute treatments. For maintenance regimens the oral or parenteral, e.g., intramuscular or subcutaneous, route is preferred. In accordance with one embodiment a composition is provided that comprises a compound of invention and albumin, e.g., a compound of the present invention, a pharmaceutically acceptable carrier and 0.1-1.0% albumin. Albumin functions as a buffer and improves the solubility of the compounds.

The invention also provides a pharmaceutical pack or kit comprising one or more containers filled with one or more of the ingredients of the pharmaceutical compositions of the invention. In accordance with one embodiment, a kit is provided for treating a patient in need of immunomodulation, including instructions for use of the kit. In this embodiment the kit comprises one or more of the S1P modulators of the invention, and may also include one or more known immunosuppressants. These pharmaceuticals can be packaged in a variety of containers, e.g., vials, tubes, microtiter well plates, bottles, and the like. Other reagents can be included in separate containers and provided with the kit; e.g., positive control samples, negative control samples, buffers, cell culture media, etc. Preferably, the kits will also include instructions for use.

The activity of compounds of the invention may be determined by using an assay for detecting S1P receptor activity (such as the [γ-35 S]GTP binding assay) and assaying for activity in the presence of S1P and the test compound. More particularly, in the method described by Traynor et al., 1995, *Mol. Pharmacol.* 47: 848-854, incorporated herein by reference, G-protein coupling to membranes can be evaluated by measuring the binding of labeled GTP.

For example, samples comprising membranes isolated from cells expressing an S1P polypeptide can be incubated in a buffer promoting binding of the polypeptide to ligand (i.e. S1P), in the presence of radiolabeled GTP and unlabeled GDP (e.g., in 20 mM HEPES, pH 7.4, 100 mM NaCl, and 10 mM $MgCl_2$, 80 pM $^{35}$S-GTPγS and 3 μM GDP), with and without a candidate modulator. The assay mixture is incubated for a suitable period of time to permit binding to and activation of the receptor (e.g., 60 minutes at 30° C.), after which time unbound labeled GTP is removed (e.g., by filtration onto GF/B filters). Bound, labeled GTP can be measured by liquid scintillation counting. A decrease of 10% or more in labeled GTP binding as measured by scintillation counting in a sample containing a candidate modulator, relative to a sample without the modulator, indicates that the candidate modulator is an inhibitor of S1P receptor activity.

A similar GTP-binding assay can be performed without the presence of the ligand (S1P) to identify agents that act as agonists. In this case, ligand-stimulated GTP binding is used as a standard. An agent is considered an agonist if it induces at least 50% of the level of GTP binding induced by S1P when the agent is present at 10 μm or less, and preferably will induce a level which is the same as or higher than that induced by the ligand.

GTPase activity can be measured by incubating cell membrane extracts containing an S1P receptor with $γ^{32}$P-GTP. Active GTPase will release the label as inorganic phosphate, which can be detected by separation of free inorganic phosphate in a 5% suspension of activated charcoal in 20 mM $H_3PO_4$, followed by scintillation counting. Controls would include assays using membrane extracts isolated from cells not expressing an S1P receptor (e.g., mock-transfected cells), in order to exclude possible non-specific effects of the candidate modulator. In order to assay for the effect of a candidate modulator on S1P-regulated GTPase activity, cell membrane samples can be incubated with the ligand (S1P), with and without the modulator, and a GTPase assay can be performed as described above. A change (increase or decrease) of 10% or more in the level of GTP binding or GTPase activity relative to samples without modulator is indicative of S1P modulation by a candidate modulator.

S1P receptor (hS1P1, hS1P3, rS1P1, rS1P3 and parental cell) $Ca^{2+}$ Flux protocol 1. Material
   a. FLIPR buffer: 1× HBSS; 10 mM HEPES
   b. Cell growth media:
      i. human and rat S1P1 and S1P3: F12-Ham's media; 10% FBS (qualified); 1× Pen/Strep/Glu; 300 ug/mL Hygromycin; 400 ug/mL Geneticin
      ii. Parental cell: human and rat S1P1 and S1P3: F12-Ham's media; 10% FBS (qualified); 1× Pen/Strep/Glu; 300 ug/mL Hygromycin;
   c. Cell seeding media; F12-Ham's media; 10% FBS (Charcoal/dextran stripped); 1× Pen/Strep/Glu;
   d. Cell dissociation buffer: Versene from Invitrogen
   e. Agonist (S1P) dissolving buffer: 0.4% (w/v) fatty-acid free BSA (Sigma # A8806) in FLIPR buffer
   f. FLIPR dye: BD PBX Calcium assay kit; Cat#641077 is composed of Calcium indicator (Cat#850000) and 100× PBX signal enhancer (cat#850001). The 100× PBX signal enhancer is diluted into FLIPR buffer 1:100 and the calcium indicator is then added at 1:1000 ratio.
   g. Cell plates (96-well): Greiner Cat#655090
   h. Compound plates (96-well): Costar #3365
   i. S1P stock solution preparation: S1P is purchased from CalBioChem (Catalog #970471; 1 mg vial; custom prep using methanol, & nitrogen gas drying inside glass vial; Storage @–20° C.). Dissolve 1 vial of S1P into 26.4 ml of agonist dissolving buffer in a 50 ml centrifuge tube; Remove label from bottle of S1P, open and drop entire bottle into tube. Sonicate at 37° for ½ hour. Clear solution of 100 μM will result. This stock solution is aliquoted and stored at –80° C.
2. Cell Line Maintenance
   a. V5 tags were added at the N-terminus of hS1P1, hS1P3, rS1P1 and rS1P3. All four genes were transfected into CHO K1 cells which stably express Gqi5.

b. hS1P1 and hS1P3 were established as stable clones and rS1P1 and rS1P3 were sorted by anti V5 tag and established as stable pools after sorting.
c. Parental cell line CHO/K1 Gqi5 is used as the control.
d. All the cells are maintained in cell growth media and splitted twice a week using Versene.
e. All the cell lines are used under passage 30.
3. Assay Protocol
a. Cell seeding: Cells are lifted from the flask by Versene and seeded in cell plates at 50K/well in cell seeding media. Cells are grown overnight at 37 degree.
b. Cell loading: Cell seeding media is discarded. Cells are loaded with 50 ul of FLIPR dye at RT for 90 min. Signal is stable for up to 5 h after dye loading.
c. Agonist (S1P) preparation: Frozen stock of S1P is thawed out and sonicated at 37° for 30 minutes every time before use. The stock is then diluted into FLIPR buffer at proper concentration.
d. Compound preparation: Compounds are dissolved in DMSO. A 3×, 10 point dilution of the compounds are carried out in DMSO. Then the compounds are diluted into assay buffer 133× so that the DMSO concentration is 0.75%.
e. Activity measurement: The fluorescence signal change of the cells upon compound addition is monitored in FLIPRtetra. 25 ul of compound is transferred into the cell plates (50 ul of FLIPR dye; DMSO concentration: 0.25%). Signal is recorded for 90 sec after compound addition. Then 50 ul of 500 nM S1P is added in the cell plate, and signal is recorded for 90 seconds upon addition.
4. Data Analysis
a. Peak value is calculated for each compound/S1P addition
b. The peak value of S1P at 200 nM is used as high control (100%), and the peak value of buffer only is used as low control (0%).
c. Data is normalized against high and low controls using the following equation:

$$POC\_S = 100*(RAW-LO)/(HI-LO)$$

d. Peak value is plotted against the concentration of compound.
e. Curve is fitted using the 4 parameter fit:

$$Y = (A + (B/(1+((x/C)^D))))$$

where: Y is POC_S (or POC)
X is compound concentration
A is the minimum (EC50min or IC50min)
B is the maxmum (EC50max or IC50max)
C is the inflection point (EC50IP or IC50IP)
D is the hill slop (EC50 slope or IC50 slope).

Identified S1P receptor agonists and antagonists can be used to treat a variety of human diseases and disorders, including, but not limited to the treatment of infections such as bacterial, fungal, protozoan and viral infections, particularly infections caused by HIV-1 or HIV-2; pain; cancers; diabetes, obesity; anorexia; bulimia; asthma; Parkinson's disease; acute heart failure; hypotension; hypertension; urinary retention; osteoporosis; angina pectoris; myocardial infarction; stroke; ulcers; asthma; allergy; benign prostatic hypertrophy; migraine; vomiting; psychotic and neurological disorders, including anxiety, schizophrenia, manic depression, depression, delirium, dementia, and severe mental retardation.

Pain is a complex subjective sensation reflecting real or potential tissue damage and the affective response to it. Acute pain is a physiological signal indicating a potential or actual injury. Chronic pain can either be somatogenetic (organic) or psychogenic. Chronic pain is frequently accompanied or followed by vegetative signs, which often result in depression.

Somatogenetic pain may be of nociceptive origin, inflammatory or neuropathic. Nociceptive pain is judged to be commensurate with ongoing activation of somatic or visceral pain-sensitive nerve fibers. Neuropathic pain results from dysfunction in the nervous system; it is believed to be sustained by aberrant somatosensory processes in the peripheral nervous system, the CNS, or both. Chronic pain results in individual suffering and social economic costs of tremendous extent. Existing pharmacological pain therapies are widely unsatisfying both in terms of efficacy and of safety.

In one embodiment, S1P modulators of the present invention are used as immunomodulators to suppress the immune system and prevent damage to healthy tissue that would otherwise occur in autoimmune diseases and in organ transplantation. The compounds can be administered to patients as part of the treatment associated with organ transplantation, including pancreas, pancreatic islets, kidney, heart and lung transplantations. The S1P modulators can be administered alone or in combination with known immunosuppressants such as cyclosporine, tacrolimus, azatioprine, desoxymetasone, cyclophosphamide, cortisone, betametasone, FK 506 (a fungal macrolide immunosuppressant), desametasone, flunisolide, prednisolone, prednisone, amcinomide desonide, methylprednisolone, triamcinolone, alclometasone and methotrexate.

The dosage to be used is, of course, dependent on the specific disorder to be treated, as well as additional factors including the age, weight, general state of health, severity of the symptoms, frequency of the treatment and whether additional pharmaceuticals accompany the treatment. The dosages are in general administered several times per day and preferably one to three times per day. The amounts of the individual active compounds are easily determined by routine procedures known to those of ordinary skill in the art S1P also acts as a survival factor in many cell types. S1P receptor modulators are anticipated to have activity in protecting cells and tissues from hypoxic conditions. In accordance with one embodiment compounds of the invention are administered to treat cells and tissues exposed to hypoxic conditions, including injury sustained as a result of ischemia. In accordance with one embodiment, the S1P modulators having antagonistic activity can be used to treat ischemia reperfusion type injury. Interference with the supply of oxygenated blood to tissues is defined as ischemia. The effects of ischemia are known to be progressive, such that over time cellular vitality continues to deteriorate and tissues become necrotic. Total persistent ischemia, with limited oxygen perfusion of tissues, results in cell death and eventually in coagulation-induced necrosis despite reperfusion with arterial blood.

The compounds of the invention and the other pharmacologically active agent may be administered to a patient simultaneously, sequentially or in combination. It will be appreciated that when using a combination of the invention, the compound of the invention and the other pharmacologically active agent may be in the same pharmaceutically acceptable carrier and therefore administered simultaneously. They may be in separate pharmaceutical carriers such as conventional oral dosage forms which are taken simultaneously. The term "combination" further refers to the case where the compounds are provided in separate dosage forms and are administered sequentially.

The compounds of the invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

An appropriate dosage level will generally be about 0.001 to 50 mg per kg patient body weight per day, which may be administered in single or multiple doses. Preferably, the dosage level will be about 0.01 to about 25 mg/kg per day; more preferably about 0.05 to about 10 mg/kg per day. For example, in the treatment or prevention of a disorder of the central nervous system, a suitable dosage level is about 0.001 to 10 mg/kg per day, preferably about 0.005 to 5 mg/kg per day, and especially about 0.01 to 1 mg/kg per day. The compounds may be administered on a regimen of 1 to 4 times per day, preferably once or twice per day.

It will be appreciated that the amount of the compound of the invention required for use in any treatment will vary not only with the particular compounds or composition selected but also with the route of administration, the nature of the condition being treated, and the age and condition of the patient, and will ultimately be at the discretion of the attendant physician.

The compositions and combination therapies of the invention may be administered in combination with a variety of pharmaceutical excipients, including stabilizing agents, carriers and/or encapsulation formulations as described herein.

Aqueous compositions of the present invention comprise an effective amount of the compounds of the invention, dissolved or dispersed in a pharmaceutically acceptable carrier or aqueous medium.

"Pharmaceutically or pharmacologically acceptable" include molecular entities and compositions that do not produce an adverse, allergic or other untoward reaction when administered to an animal, or a human, as appropriate. "Pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For human administration, preparations should meet sterility, pyrogenicity, general safety and purity standards as required by FDA Office of Biologics standards.

The compositions and combination therapies of the invention will then generally be formulated for parenteral administration, e.g., formulated for injection via the intravenous, intramuscular, subcutaneous, intralesional, or even intraperitoneal routes. The preparation of an aqueous composition that contains a composition of the invention or an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Therapeutic or pharmacological compositions of the present invention will generally comprise an effective amount of the component(s) of the combination therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including cremes, lotions, mouthwashes, inhalants and the like.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for intramuscular injection is also contemplated. In this regard, the use of DMSO as solvent is preferred as this will result in extremely rapid penetration, delivering high concentrations of the active compound(s) or agent(s) to a small area.

The use of sterile formulations, such as saline-based washes, by surgeons, physicians or health care workers to cleanse a particular area in the operating field may also be particularly useful. Therapeutic formulations in accordance with the present invention may also be reconstituted in the form of mouthwashes, or in conjunction with antifungal reagents. Inhalant forms are also envisioned. The therapeutic formulations of the invention may also be prepared in forms suitable for topical administration, such as in cremes and lotions.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. One dosage could be dissolved in 1 mL of isotonic NaCl solution and either added to 1000 mL of hypodermolysis fluid or injected at the proposed site of infusion, (see for example, *Remington's Pharmaceutical Sciences* 15th Edition, pages 1035-1038 and 1570-1580).

In certain embodiments, active compounds may be administered orally. This is contemplated for agents which are generally resistant, or have been rendered resistant, to proteolysis by digestive enzymes. Such compounds are contemplated to include chemically designed or modified agents; dextrorotatory peptides; and peptide and liposomal formulations in time release capsules to avoid peptidase and lipase degradation.

Pharmaceutically acceptable salts include acid addition salts and which are formed with inorganic acids such as, for example, hydrochloric, hydrobromic, boric, phosphoric, sulfuric acids or phosphoric acids, or such organic acids as acetic, oxalic, tartaric, maleic, fumaric, citric, succinic, mesylic, mandelic, succinic, benzoic, ascorbic, methanesulphonic, a-keto glutaric, a-glycerophosphoric, glucose-1-phosphoric acids and the like. Salts formed with the free carboxyl groups can also be derived from inorganic bases such as, for example, sodium, potassium, ammonium, calcium, magnesium, or ferric hydroxides, and such organic bases as isopropylamine, trimethylamine, histidine, procaine and the like. Other examples of pharmaceutically acceptable salts include quaternary derivatives, and internal salts such as N-oxides.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze drying techniques which yield a powder of the active ingredient plus any additional desired ingredient from a previously sterile-filtered solution thereof.

The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

In addition to the compounds formulated for parenteral administration, such as intravenous or intramuscular injection, other pharmaceutically acceptable forms include, e.g. tablets or other solids for oral administration; liposomal formulations; time-release capsules; and any other form currently used, including cremes.

Additional formulations suitable for other modes of administration include suppositories. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders.

In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor.

The pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the invention may be incorporated for administration orally or by injection include aqueous solution, suitably flavored syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For treating clinical conditions and diseases noted above, the compound of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The following examples are given for the purpose of illustrating the invention, but not for limiting the scope or spirit of the invention.

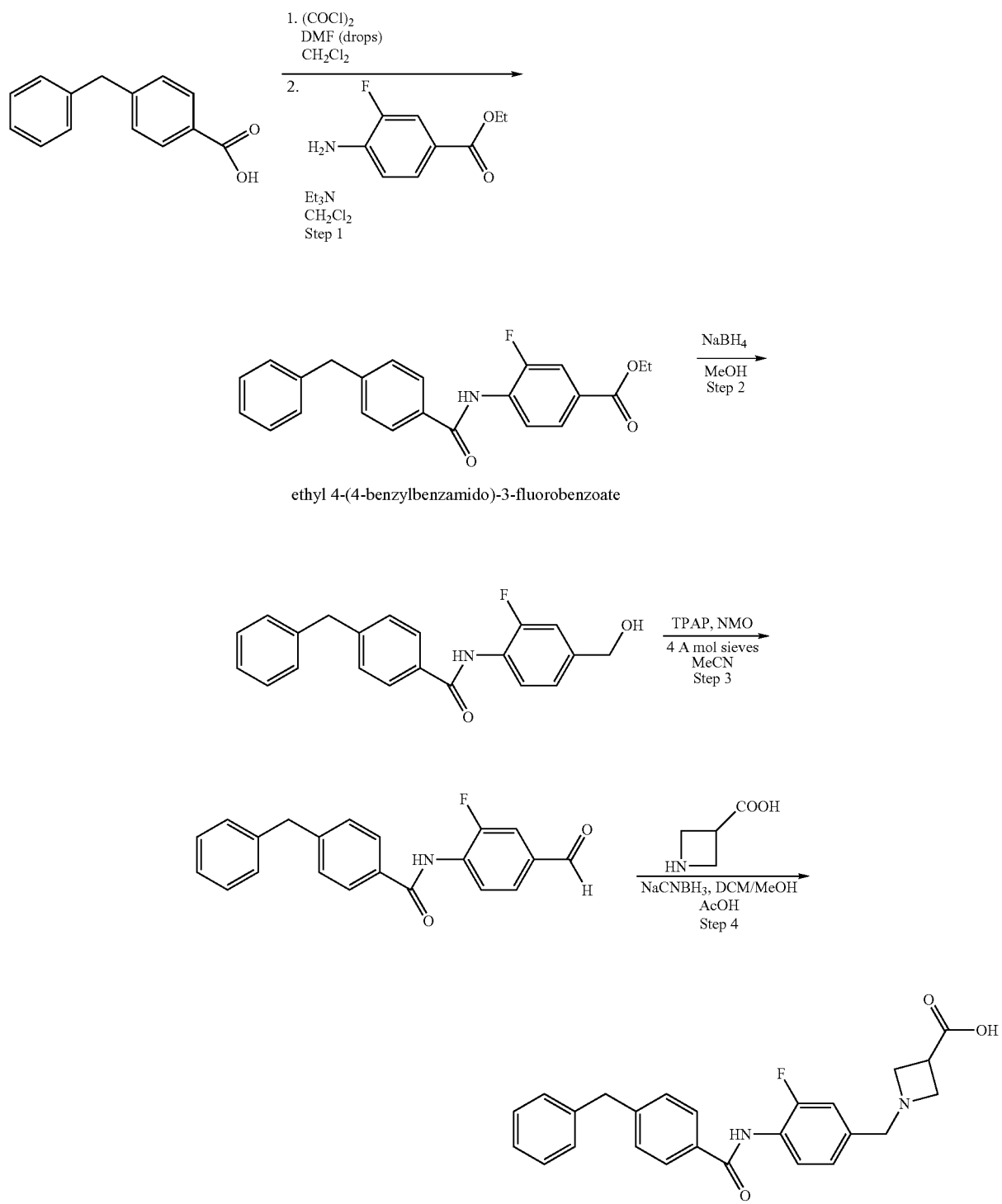

General Procedure of Reductive Amination

A mixture of aldehyde (1.0 mmol), acetic acid (1.5 mmol) and azetidine-3-carboxylic acid or piperidine-4-carboxylic acid (1.2-1.5 mmol) in dichloromethane (DCM)/MeOH (1:1, 10 mL) was stirred at room temperature for 1 h. Sodium cyanoborohydride (0.5 mmol) was added and the reaction mixture was stirred for 2-3 h at room temperature. After concentration of solvent under reduced pressure, the resulting residue was dissolved in DMSO, filtered and purified by reverse phase preparative HPLC (Phenomenex reverse phase Luna 5u C18(2) column, 60×21.2 mm ID, mobile phase: A=0.05% TFA in water; B=0.05% trifluoroacetic acid (TFA) in acetonitrile. The flow rate was 10-12 mL/minute) to yield the desired final product with puritiy greater than 95%. All final products were obtained as the TFA salts unless stated otherwise. Alternatively, the crude mixture of reductive amination can be purified by trituration with MeOH and water.

Example 1

1-(4-(4-Benzylbenzamido)-3-fluorobenzyl)azetidine-3-carboxylic acid

Ethyl 4-(4-benzylbenzamido)-3-fluorobenzoate

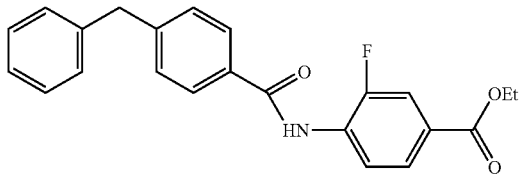

A solution of 4-benzylbenzoic acid (1.06 g, 5 mmole) in dichloromethane (10 mL) was added oxalyl dichloride (1 mL) followed by a few drops of DMF at 0° C. The resulting mixture was stirred room temperature for 3 hours. Removal of the solvents gave the residue which was dissolved in dichloromethane (2 mL) and added to the solution of triethylamine (1.4 mL, 10 mmol) and ethyl 4-amino-3-fluorobenzoate (916 mg, 5 mmole) in dichloromethane (50 mL) at 0° C. After stirring at room temperature for 48 hours, the mixture was washed with saturated sodium bicarbonate and 1 N HCl. The combined organic extracts were washed with brine, dried and concentrated under reduced pressure to give the residue which was purification by silica gel chromatography on ISCO system. The desired product was obtained as an off white solid: $^1$H NMR (400 MHz, CDCl$_3$) δ 8.63 (t, J=8.8 Hz, 1H), 8.20 (s, 1H), 7.83 (m, 4H), 7.18-7.35 (m, 6H), 4.39 (q, J=7.2 Hz, 1H), 4.07 (s, 2H), 1.40 (t, J=7.2 Hz, 3H).

4-Benzyl-N-(2-fluoro-4-(hydroxymethyl)phenyl)benzamide

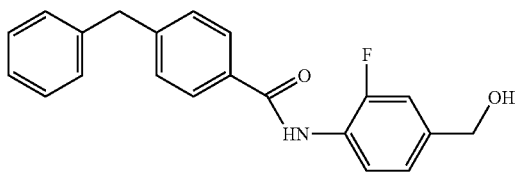

A solution of methyl ethyl 4-(4-benzylbenzamido)-3-fluorobenzoate (100 mg, 0.265 mmol) in MeOH (10 mL) at room temperature was added sodium borohydride (200 mg, 5.3 mmol). The mixture was stirred at room temperature for 3 days. Removal of the solvent gave the residue which was diluted with EtOAc (50 mL) and washed with 1 N NaOH and brine. The organic layer was separated, dried and concentrated. The residue was purified on ISCO system (1% methanol in dichloromethane) to give a pure product as a white crystalline. $^1$H NMR (400 MHz, CDCl$_3$) δ 8.44 (t, J=8.0 Hz, 1H), 8.02 (s, 1H), 7.80 (d, J=8.4 Hz, 2H), 7.15-7.34 (m, 8H), 4.69 (d, J=6.0 Hz, 1H), 4.06 (s, 2H).

4-Benzyl-N-(2-fluoro-4-formylphenyl)benzamide

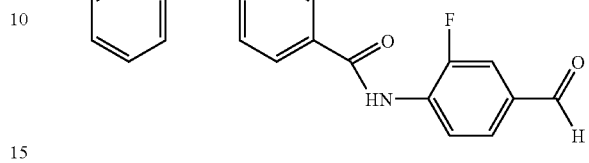

A mixture of 4-benzyl-N-(2-fluoro-4-(hydroxymethyl)phenyl)benzamide (200 mg, 0.60 mmol), 4-methylmorpholine N-oxide (140 mg, 1.2 mmol), and 4 A molecular sieves (1 g) in 10 ml of CH$_3$CN was treated with tetrapropylammonium perruthnate (10 mg, 0.03 mmol) and the resulting mixture was stirred at room temperature for 12 hours. The solids were filtered and the filtrated was concentrated. The residue was purified on ISCO system (80% hexane in dichloromethane) to give a pure product as a white crystalline: $^1$H NMR (400 MHz, CDCl$_3$) δ 9.93 (s, 1H), 8.80 (t, J=8.0 Hz, 1H), 8.25 (s, 1H), 7.84 (d, J=7.2 Hz, 2H), 7.74 (d, J=8.4 Hz, 1H), 7.69 (d, J=10.8 Hz, 1H), 7.19-7.37 (m, 6H), 4.07 (s, 2H).

1-(4-(4-Benzylbenzamido)-3-fluorobenzyl)azetidine-3-carboxylic acid

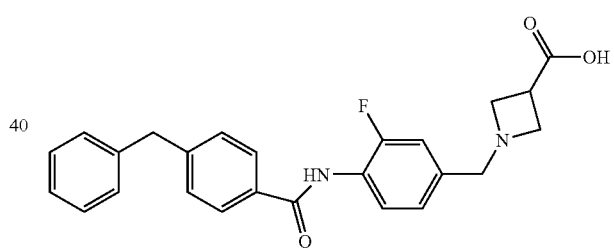

The title compound was prepared by the general method for reductive amination to give the title compound: $^1$H NMR (400 MHz, CD$_3$OD) δ 7.86-7.94 (m, 4H), 7.17-7.39 (m, 8H), 4.42 (s, 2H), 4.33 (m, 4H), 4.06 (s, 2H), 3.71 (m, 1H). $^{19}$F NMR (376 MHz, CD$_3$OD) δ −77.4 (TFA), −123.4. MS (ESI) m/z: Calculated: 418.46; Observed: 419.0 (M$^+$+1).

Scheme 2

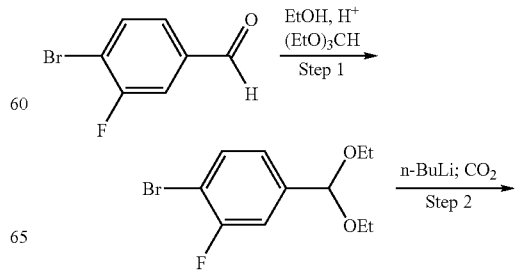

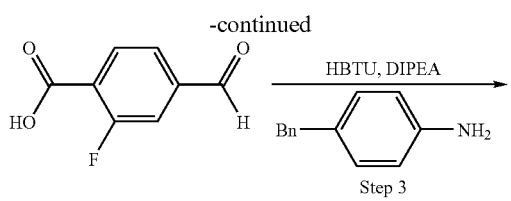

Step 3

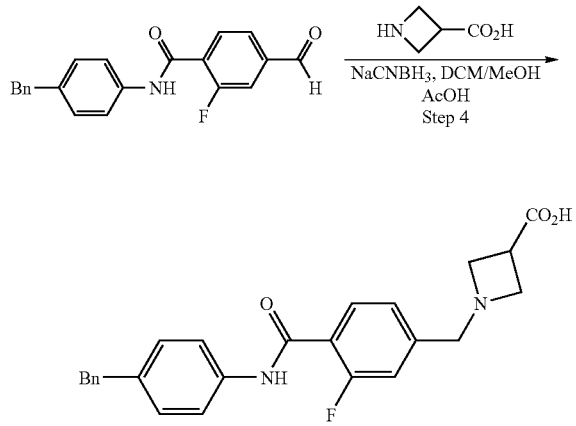

Example 2

1-(4-((4-benzylphenyl)carbamoyl)-3-fluorobenzyl)azetidine-3-carboxylic acid

1-Bromo-4-(diethoxymethyl)-2-fluorobenzene

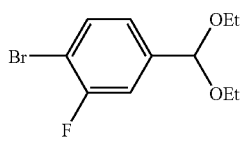

To a solution of 3-fluoro-4-bromobenzaldehyde (20.0 g, 98.5 mmol) in dry EtOH (120 mL) was added acetyl chloride (2.04 mL, 29.6 mmol) followed by the addition of triethyl orthoformate (6.55 mL, 39.4 mmol) and the contents were heated to 70° C. for 3 h. The contents were cooled to room temperature and shifted to a rotary evaporator and subjected to reduced pressure (280 mm Hg) with bath temperature 65° C. for 45 min. The pressure was further lowered to remove all the solvent. To this mixture, fresh Ethanol (60 mL), acetyl chloride (1.5 mL), triethyl orthoformate (5.0 mL) and heated to 70° C. for 2 h. The solvent was removed under the reduced pressure and diluted with EtOAc (200 mL), washed with saturated sodium bicarbonate (3×100 mL), brine and dried over anhydrous sodium sulfate. The solvent was evaporated and the residue purified by silica gel column (basified with 5% Et$_3$N, eluent: EtOAc/hexanes, 1/20) to afford 1-bromo-4-(diethoxymethyl)-2-fluorobenzene as a colorless oil. 1H NMR (400 MHz, CDCl$_3$) δ ppm 8.03 (t, J=8.1 Hz, 1H), 7.36-7.33 (m, 2H), 5.54 (s, 1H), 3.63-3.52 (m, 4H), 1.25 (m, 6H).

2-Fluoro-4-formylbenzoic acid

To a solution of 1-bromo-4-(diethoxymethyl)-2-fluorobenzene (10.12 g, 36.53 mmol) in dry THF (90 mL) cooled to −78° C. was added n-butyllithium (2.5 M in hexanes, 16.5 mL, 43.83 mmol) was added dropwise over a period of 10 min. The contents were further stirred for 30 min and CO$_2$ was bubbled through the mixture for 0.5 h. (exothermic). The cooling bath was removed and the contents warmed to room temperature. The mixture was treated with aqueous NaOH (1N, 100 mL) and washed with EtOAc. The aqueous layer was acidified to pH 2 with HCl (5N) and the free acid was extracted with EtOAc (3×75 mL). The combined organic layers were washed with water and brine, dried over MgSO$_4$ and evaporated. The residue was dissolved in ether (30 mL), TFA (1.5 mL) and water (2.0 mL) and stirred overnight. The volatiles were removed under reduced pressure and co-evaporated with toluene. The residue was then treated with diethyl ether (75 mL) and filtered. The filter cake was dried under vacuum without further purification to give 2-fluoro-4-formylbenzoic acid as a white solid. 1H NMR (400 MHz, DMSO-d6) δ ppm 13.48 (s, 1H), 10.06 (s, 1H), 8.06 (t, J=7.4 Hz, 1H), 7.84-7.79 (m, 2H). MS (ESI) m/z: Calculated: 168.0; Observed: 167.0 (M⁻−1).

N-(4-benzylphenyl)-2-fluoro-4-formylbenzamide

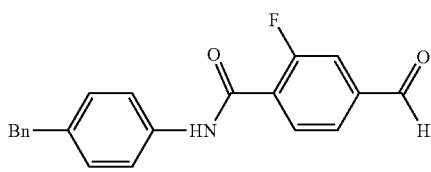

To a solution of 4-benzylbenzenamine (0.100 g, 0.55 mmol), 2-fluoro-4-formylbenzoic acid (0.092 g, 0.55 mmol), N,N-diethylpropan-2-amine (0.10 ml, 0.65 mmol) in DMF (2.00ml) was added HBTU. The reaction mixture was stirred at room temperature for 1 h. The mixture was diluted with EtOAc, washed with water and dried over MgSO$_4$. The solvent was evaporated and the residue was purified by flash chromatography in a EtOAc/Hexene system to give the title compound. MS (ESI) m/z: Calculated; 333.3: Observed; 332.1. 1H NMR (300 MHz, CHLOROFORM-d) δ ppm 10.05-10.10 (1H, m), 8.31-8.44 (2H, m), 7.80-7.85 (1H, m), 7.67-7.73 (1H, m), 7.56-7.62 (2H, m), 7.15-7.40 (6H, m), 3.99 (2H, s)

35
1-(4-((4-benzylphenyl)carbamoyl)-3-fluorobenzyl)azetidine-3-carboxylic acid
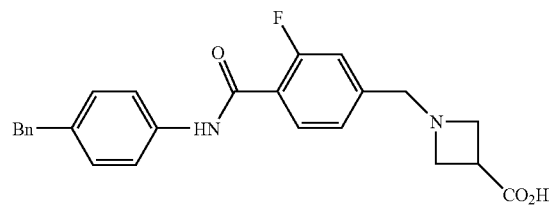
The compound was prepared by the general method for reductive amination to give the title compound. MS (ESI) m/z: Calculated; 418.46: Observed; 419.1. 1H NMR (300 MHz, DMSO-$d_6$) δ ppm 10.25-10.34 (1H, m), 7.51-7.67 (3H, m), 7.09-7.33 (8H, m), 3.87-3.94 (2H, s), 3.56-3.63 (2H, s), 3.38 (2H, br. s.), 3.17 (3H, m.)
Scheme 3
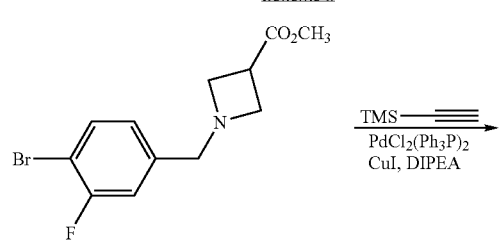
Scheme 4
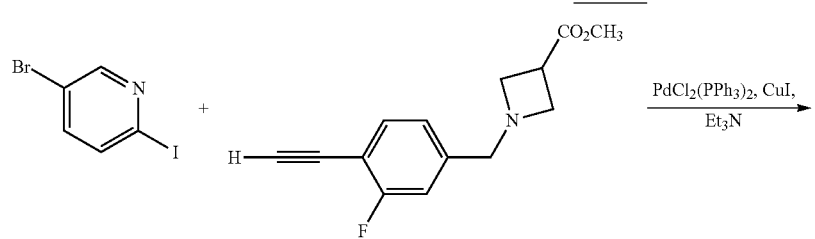
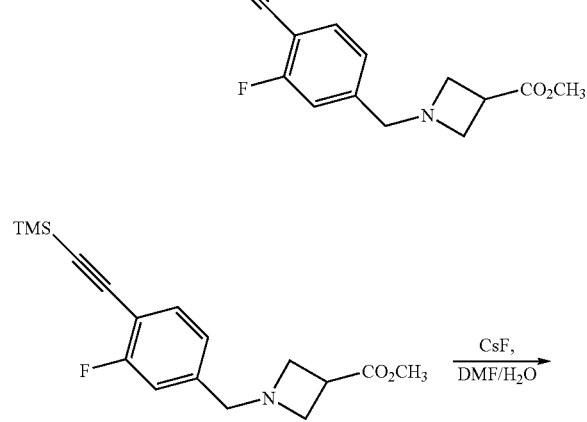
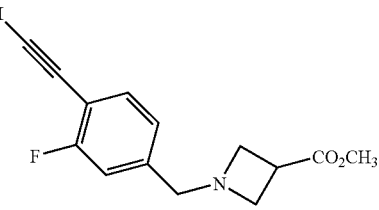
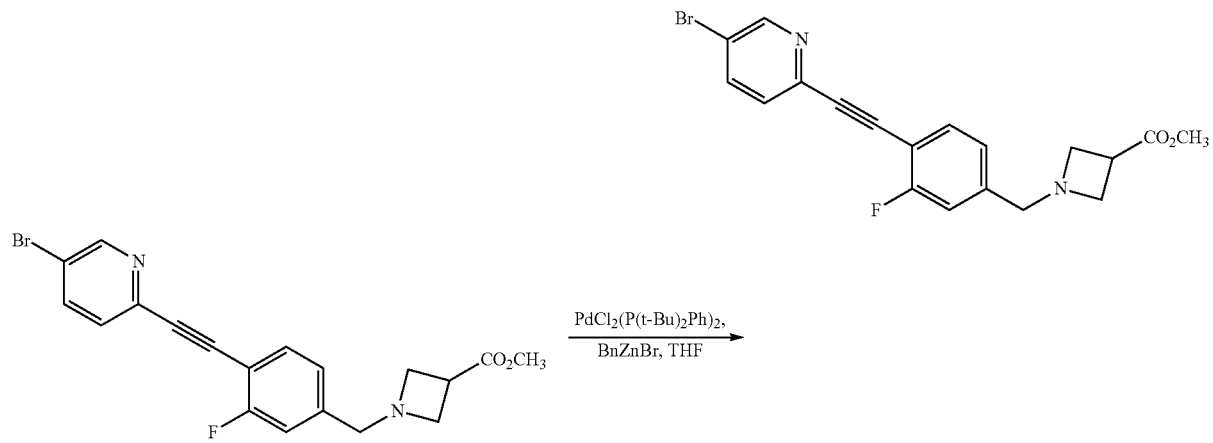

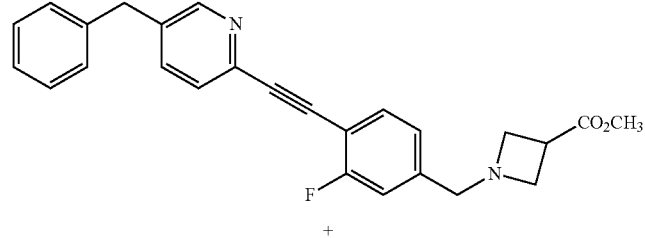
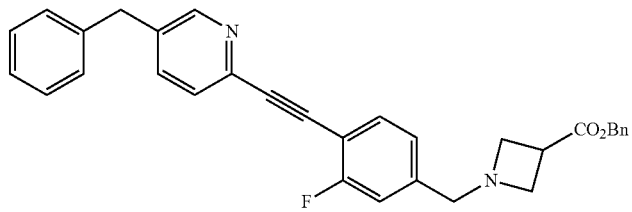
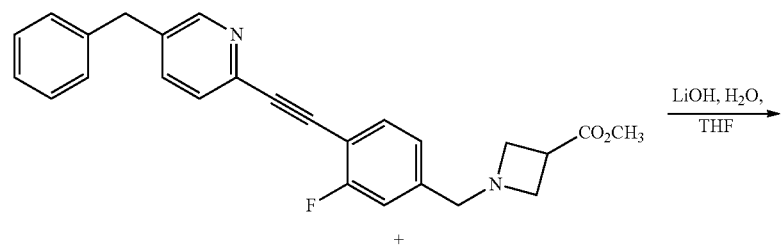
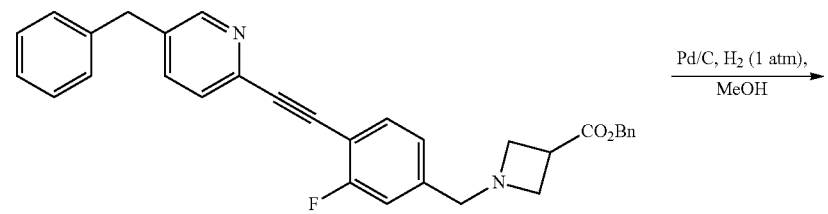
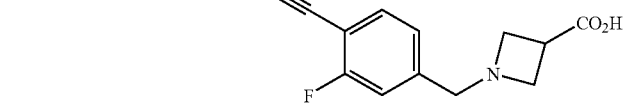
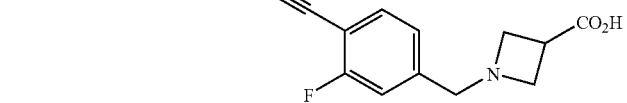

Example 3

Methyl 1-(4-ethynyl-3-fluorobenzyl)azetidine-3-carboxylate

Methyl 1-(4-bromo-3-fluorobenzyl)azetidine-3-carboxylate

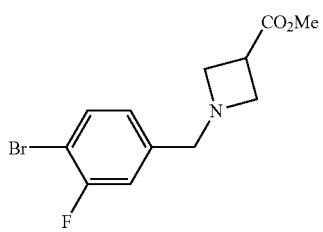

Azetidine-3-carboxylic acid (43 g, 421 mmol), 4-bromo-3-fluorobenzaldehyde (81.4 g, 401 mmol), methyl orthoformate (219 mL, 2005 mmol), and AcOH (34 mL, 601 mmol) were added to DCM (700 mL) at rt under an $N_2$ atmosphere. The mixture was stirred for 15 min, at which point sodium triacetoxyborohydride (127 g, 601 mmol) was added portionwise (exothermic). After 2 h, solvent swap with MeOH (257 g, 8019 mmol), and sulfuric acid (79 g, 802 mmol) was added slowly (exothermic). The mixture was heated at reflux for 18 h. Solvent was removed and the mixture was extracted using DCM and water. The organic layer was purified using a Biotage column (isopropanol/heptane), affording methyl 1-(4-bromo-3-fluorobenzyl)azetidine-3-carboxylate as a clear oil. MS (ESI) m/z: Calculated: 301.0; Observed: 302.0 ($M^+$+1).

Methyl 1-(3-fluoro-4-(2-(trimethylsilyl)ethynyl)benzyl)azetidine-3-carboxylate

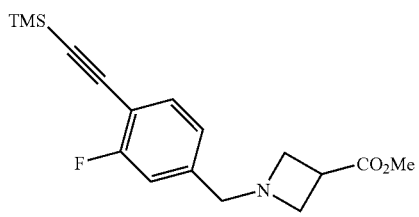

Methyl 1-(4-bromo-3-fluorobenzyl)azetidine-3-carboxylate (25.00 g, 82.7 mmol), copper (I) iodide (3.14 g, 16.5 mmol), (trimethylsilyl)acetylene (81.9 mL, 579 mmol), bis(triphenylphosphine)palladium(II) chloride (5.81 g, 8.27 mmol), and Hunig's base (115 mL, 662 mmol) were combined in a sealable tube along with 100 mL THF. The tube was sealed and heated to 80 deg. C. under vigorous stirring for 24 h. The mixture was then cooled to room temperature, filtered, and evaporated. The resulting oil was purified by Biotage (75 L, 0-50% EtOAc/hexanes), affording methyl 1-(3-fluoro-4-(2-(trimethylsilyl)ethynyl)benzyl)azetidine-3-carboxylate as a transparent brown oil. MS (ESI) m/z: Calculated: 319.1; Observed: 320.1 ($M^+$+1).

Methyl 1-(4-ethynyl-3-fluorobenzyl)azetidine-3-carboxylate

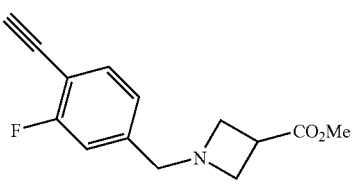

Methyl 1-(3-fluoro-4-(2-(trimethylsilyl)ethynyl)benzyl)azetidine-3-carboxylate (20.9 g, 65 mmol) and cesium fluoride (11 g, 72 mmol) were added to DMF (50 mL). MeOH (100 mL) was added. After 2 h, MeOH was removed and the mixture was extracted with DCM and water. The organic layer was washed with brine and dried over magnesium sulfate. The solvent was removed and the material was purified by Biotage (75 L, 7-100% EtOAc/hexanes), affording methyl 1-(4-ethynyl-3-fluorobenzyl)azetidine-3-carboxylate as light yellow oil. MS (ESI) m/z: Calculated: 247.1; Observed: 248.0 ($M^+$+1). 1-(4-(2-(5-Benzylpyridin-2-yl)ethynyl)-3-fluorobenzyl)azetidine-3-carboxylic acid and 1-(4-(2-(5-Benzylpyridin-2-yl)ethyl)-3-fluorobenzyl)azetidine-3-carboxylic acid

Methyl 1-(4-(2-(5-bromopyridin-2-yl)ethynyl)-3-fluorobenzyl)azetidine-3-carboxylate

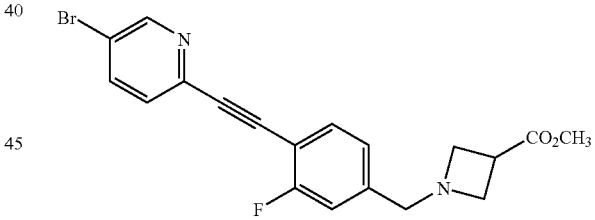

A solution of 5-bromo-2-iodopyridine (800 mg, 2818 μmol), methyl 1-(4-ethynyl-3-fluorobenzyl)azetidine-3-carboxylate (704 mg, 2846 μmol), and copper(I) iodide (21.5 mg, 113 μmol) in triethylamine (9.4 mL) was sparged with argon (30 sec), and PdCl$_2$(PPh$_3$)$_2$ (79.1 mg, 113 μmol) was then added in one portion at 25° C. The reaction mixture was cooled to 0° C. and stirred for 40 min, and then allowed to stir at 25° C. for 1.5 h. The mixture was subsequently diluted with EtOAc (120 mL) and sequentially washed with water (4×30 mL) and brine (30 mL). The organic layer was dried over sodium sulfate, filtered, and concentrated in vacuo. Chromatographic purification of the residue (silica gel, 0-100% EtOAc/Hexanes) furnished methyl 1-(4-(2-(5-bromopyridin-2-yl)ethynyl)-3-fluorobenzyl)azetidine-3-carboxylate as a light yellow oil. MS (ESI) m/z: Calculated: 402.0/404.0; Observed: 402.8/404.8 ($M^+$+1).

Methyl 1-(4-(2-(5-benzylpyridin-2-yl)ethynyl)-3-fluorobenzyl)azetidine-3-carboxylate

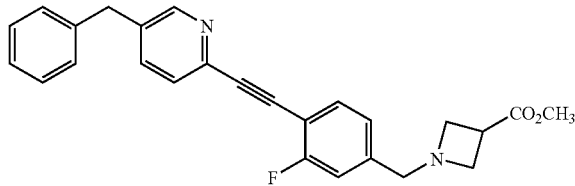

Benzyl 1-(4-(2-(5-benzylpyridin-2-yl)ethynyl)-3-fluorobenzyl)azetidine-3-carboxylate

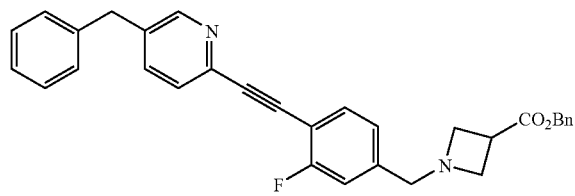

Methyl 1-(4-(2-(5-bromopyridin-2-yl)ethynyl)-3-fluorobenzyl)azetidine-3-carboxylate (340.0 mg, 843 μmol), PdCl$_2$(P(t-Bu)$_2$Ph)$_2$ (37 mg, 59 μmol), and THF (4.0 mL) were combined under an argon atmosphere. Benzylzinc(II) bromide (0.5M in THF; 1.92 mL, 961 μmol) was added via syringe, and the resulting solution was stirred at 25° C. for 1 h. Additional benzylzinc(II) bromide (0.5M in THF; 1.92 mL) was then added, and the resulting solution was stirred for 1 h at 25° C. A third portion of benzylzinc(II) bromide (0.5M in THF; 1.92 mL) was then added, and the resulting solution was stirred for 1 h at 25° C. The mixture was subsequently partitioned between half-saturated aqueous NaHCO$_3$ (50 mL) and EtOAc (100 mL). The organic layer was separated, washed with brine (30 mL), dried over Na$_2$SO$_4$, filtered, and concentrated in vacuo. Chromatographic purification of the residue (silica gel, 0-100% EtOAc/Hexanes) separately furnished benzyl 1-(4-(2-(5-benzylpyridin-2-yl)ethynyl)-3-fluorobenzyl)azetidine-3-carboxylate (MS (ESI) m/z: Calculated: 490.2; Observed: 490.8 (M$^+$+1)) and methyl 1-(4-(2-(5-benzylpyridin-2-yl)ethynyl)-3-fluorobenzyl)azetidine-3-carboxylate (MS (ESI) m/z: Calculated: 414.2; Observed: 414.8 (M$^+$+1)) as a yellow oils.

1-(4-(2-(5-Benzylpyridin-2-yl)ethynyl)-3-fluorobenzyl)azetidine-3-carboxylic acid

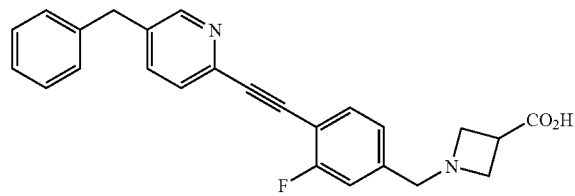

A mixture of lithium hydroxide hydrate (28.4 mg, 677 μmol) and methyl 1-(4-(2-(5-benzylpyridin-2-yl)ethynyl)-3-fluorobenzyl)azetidine-3-carboxylate (77.9 mg, 188 μmol) in THF (2.7 mL) and water (0.69 mL) was stirred at 25° C. for 3 h. The reaction mixture was then partially concentrated in vacuo (to remove THF), water (1.5 mL) was added, and the resulting solution was sonicated for 1 min. The reaction solution was subsequently acidified with 1.0N HCl (670 μL), brought to pH 6 with 1M Na$_2$HPO$_4$/NaH$_2$PO$_4$ phosphate buffer (1.0 mL), and sonicated. The resulting precipitate was collected by vacuum filtration, washed with water (3.0 mL), and dried in vacuo to provide 1-(4-(2-(5-benzylpyridin-2-yl)ethynyl)-3-fluorobenzyl)azetidine-3-carboxylic acid as a light yellow solid. MS (ESI) m/z: Calculated: 400.2; Observed: 401.1 (M$^+$+1).

Example 4

1-(4-(2-(5-Benzylpyridin-2-yl)ethyl)-3-fluorobenzyl)azetidine-3-carboxylic acid

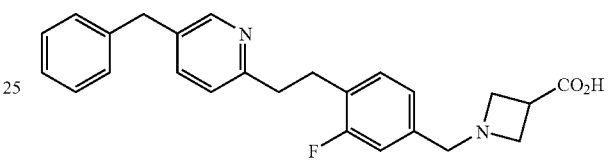

A mixture of benzyl 1-(4-(2-(5-benzylpyridin-2-yl)ethynyl)-3-fluorobenzyl)-azetidine-3-carboxylate (103.0 mg, 210 μmol) and 10% palladium on carbon (22 mg, 21 μmol) in MeOH (4.0 mL) was cycled under an H$_2$ atmosphere (alternately evacuating flask to 1 Torr, then refilling with H$_2$ (1 atm); repeated 3×), then stirred under H$_2$ (1 atm) at 25° C. for 5 h. The reaction suspension was subsequently filtered through Celite (washing with MeOH (10 mL)), and the filtrate was concentrated in vacuo. rpHPLC purification of the residue (C18, 0-100% CH$_3$CN/H$_2$O+0.1% TFA) furnished 1-(4-(2-(5-benzylpyridin-2-yl)ethyl)-3-fluorobenzyl)azetidine-3-carboxylic acid, bis(trifluoroacetic acid) salt as a colorless oil. MS (ESI) m/z: Calculated: 404.2; Observed: 405.1 (M$^+$+1).

Example 5

1-(4-(2-(5-Benzyl-2-(methylamino)phenyl)ethynyl)-3-fluorobenzyl)azetidine-3-carboxylic acid

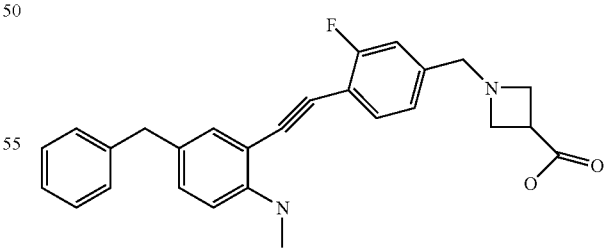

The title compound can be made using methods similar to those in Example 3. MS m/z: Calculated 428.19: Observed: 429.2.

Activity of Compounds of the Invention

The compounds of the invention made according to the synthesis noted above can be assayed for their ability to modulate the S1P-1 receptor. Compounds can be evaluated for the ability to induce S1P1-specific receptor internalization using standard in-vitro receptor internalization assays and their utility as immunoregulatory agents can be demonstrated by their activity as agonists of the S1P1 receptor measured in the receptor internalization assay (>50% of S1P control at 10 nM or 300 nM). The compounds accordingly are expected to be useful as S1P-1 receptor modulators, e.g., in the treatment of a variety of S1P-1 receptor-mediated clinical conditions. Such conditions include transplant rejection (solid organ transplant and islet cells); transplant rejection (tissue); cancer; autoimmune/inflammatory diseases; rheumatoid arthritis; lupus; insulin dependent diabetes (Type I); non-insulin dependent diabetes (Type II); multiple sclerosis; psoriasis; ulcerative colitis; inflammatory bowel disease; Crohn's disease; acute and chronic lymphocytic leukemias and lymphomas.

To further demonstrate the suitability of compounds of the invention as S1P-1 receptor modulators for treating conditions such as transplant rejection; cancer; autoimmune/inflammatory diseases; rheumatoid arthritis; lupus; diabetes; multiple sclerosis; psoriasis; ulcerative colitis; inflammatory bowel disease; Crohn's disease; acute and chronic lymphocytic leukemias and lymphomas where immunosuppression is central (of which reduction of lymphopenia is therefore a well-established indicator), compounds of the invention can be evaluated in laboratory animals as described below.

Protocol

Mice

C57BL/6J mice (B6, Jackson Laboratories, Bar Harbor, Me. can be maintained in a specific pathogen-free environment under a microisolator containment system. Both adult male and female age-matched mice can be used for all experiments, which can be reviewed and approved by the Animal Care and Use Committee at the University of Virginia. Whenever the protocol stated Mice were anesthetized via intraperitoneal injections of ketamine hydrochloride (125 mg/kg; Sanofi Winthrop Pharmaceuticals, New York, N.Y.), xylazine (12.5 mg/kg TranquiVed; Phoenix Scientific, St. Joseph, Mo.), and atropine sulfate (0.025 mg/kg; Fujisawa USA, Deerfield, Ill.).

Flow Cytometry Preparation and Analysis

Blood can be harvested from at least six mice for each time point of 0, 4, 8, 24, 48, 72 h following one day, 3 days or 7 days daily dosing with the test compound. Following terminal bleeds brain and certain other tissues can be harvested from all animals undergoing treatment. Cell counts can be determined from whole blood, yielding cell counts in thousands of cells per microliter (K/lL).

To identify and quantify lymphocyte subsets, cell suspensions were analyzed by flow cytometry. Following red blood cell lysis, cells were stained with anti-mouse monoclonal antibodies against CD3, CD4, CD8, CD19, and NK1.1 (BD Biosciences, San Jose, Calif.). Cells were analyzed via four-color flow cytometry on a FACSCalibur (BD Biosciences) in the University of Virginia Cancer Center Core Facility. Lymphocyte subsets, including B cells, total T cells, CD4 T cells, CD8 T cells, double-positive thymocytes, double-negative thymocytes. NK cells, and NK/T cells. were analyzed. The size of each cell population was calculated as the product of the total lymphocyte count recorded by the Hemavet or hemocytometer and the percentage of positive lymphocytes recorded by the flow cytometer. All data were analyzed with BD Biosciences Cell Quest analysis software.

The compounds of the invention are expected to be useful drugs for treating conditions such as transplant rejection; cancer; autoimmune/inflammatory diseases; rheumatoid arthritis; lupus; diabetes; multiple sclerosis; psoriasis; ulcerative colitis; inflammatory bowel disease; Crohn's disease; acute and chronic lymphocytic leukemias and lymphomas where immunosuppression is central.

Rat Lymphopenia Study Protocol

Animals:

Female Lewis rats (150-175 gms, 6-8 wks) are received from Charles River Laboratories and allowed to acclimatize for at least one week before being placed on study.

Procedure:

1) Rats (n=4/group) are administered compound or vehicle (12.5% captisol in water) orally (PO, 10 mL/kg) at time 0.

2) At various time points following dosing (1, 4, 8, or 24 hrs), animals are sacrificed by CO2 inhalation.

3) Using a 20 G needle and 1 cc syringe, blood is collected by cardiac puncture.

4) Approximately 500 µL of blood is placed in a microtainer tube containing EDTA (BD #365973), and the sample is mixed thoroughly.

5) Differential cell counts are performed using an Advia 120 hematology system by Bayer.

Equivalents

Those skilled in the art will recognize, or be able to ascertain using no more than routine experimentation, numerous equivalents to the specific procedures described herein. Such equivalents are considered to be within the scope of the invention. Various substitutions, alterations, and modifications may be made to the invention without departing from the spirit and scope of the invention. Other aspects, advantages, and modifications are within the scope of the invention. The contents of all references, issued patents, and published patent applications cited throughout this application are hereby incorporated by reference. The appropriate components, processes, and methods of those patents, applications and other documents may be selected for the invention and embodiments thereof.

What is claimed is:

1. A compound having the formula

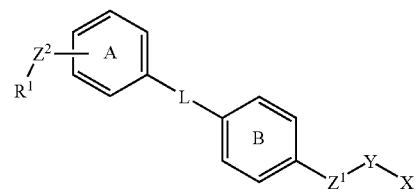

or a pharmaceutically-acceptable salt thereof, wherein:
A is phenyl substituted with 0, 1, 2 or 3 substituents selected from F, Cl, Br, $OC_{1-4}$alk, $C_{1-4}$alk, and $C_{1-4}$haloalk;
B is phenyl substituted with 0, 1, 2 or 3 substituents selected from F, Cl, Br, $OC_{1-4}$alk, $C_{1-4}$-alk, and $C_{1-4}$haloalk;
L is —C≡C—, —CH$_2$CH$_2$—, —N(R$^a$)C(=O)— or —C(=O)N(R$^a$)—;
$R^a$ is, independently in each instance, H or $C_{1-6}$alk;
$R^1$ is selected from $C_{1-6}$alk, $OC_{1-5}$alk, $N(R^a)C_{1-5}$ alk, $N(C_{1-5}alk)C_{1-5}$alk, aryl and heteroaryl;
X is selected from $WC(=O)OR^{6a}$, $WP(=O)R^{6b}R^{6c}$, $WS(=O)_2OH$, $WCONHSO_3H$ and 1H-tetrazol-5-yl;
W is a direct bond, oxygen or $C_{1-4}$alk having one or more substituents independently selected from halogen, OH, cyano, $NR^aR^a$, arylamino, heteroarylamino, $OC_{1-4}$alk and $CO_2H$;
$R^{6a}$ is hydrogen or $C_{1-4}$alk;

$R^{6b}$ and $R^{6c}$ are independently hydrogen, OH, $C_{1-4}$alk or $C_{1-4}$haloalk;

Y is residue of formula (a) wherein the left and right asterisks indicate the point of attachment (a)

wherein the N, designated by the left asterisk, is attached to $Z^1$, and the carbon, designated by the right asterisk, is attached to X,
wherein
- Q is selected from a direct bond, C=O, C=S, SO$_2$, C=ONR$^a$ and (CR$^{10}$R$^{11}$)$_m$;
- m is 0, 1, 2 or 3;
- $R^7$ and $R^8$ together with the atoms to which they are attached form a 4- to 7-membered ring optionally containing an additional heteroatom selected from N, O and S;
- $R^9$ is selected from hydrogen, halogen, OH, cyano, $C_{1-6}$alk, $SC_{1-5}$alk, $OC_{1-5}$alk, $C_{1-6}$haloalk and $OC_{1-5}$haloalk;
- $R^{10}$ and $R^{11}$ are independently selected from hydrogen, halogen, OH, cyano, $C_{1-6}$alk, $OC_{1-5}$alk, $SC_{1-5}$alk, $C_{1-6}$haloalk and $OC_{1-5}$haloalk;
- $Z^2$ is selected from O, NR$^3$, S, S(=O), S(=O)$_2$, (CR$^4$R$^5$)$_n$, C=O, C=S, C=N—R$^3$, and a direct bond, wherein n is 0, 1, 2 or 3;
- $Z^1$ is selected from O, NR$^3$, S, S(=O), S(=O)$_2$NR$^3$, (CR$^4$R$^5$)$_n$, C=O, C=S, and C=N—R$^3$, wherein n is 1, 2 or 3;
- $R^3$ is selected from hydrogen, OH, SO$_2$, C=O, C=S, C=NH, $C_{1-6}$alk, $OC_{1-5}$alk, $SC_{1-5}$alk, $C_{1-6}$haloalk, $OC_{1-5}$haloalk, aryl and heteroaryl; or when $Z^2$ is a direct bond, $R^3$ is a $C_3$-$C_6$ ring optionally containing a heteroatom; and
- $R^4$ and $R^5$ are independently selected from hydrogen, halogen, OH, cyano, $C_{1-6}$alk, $OC_{1-5}$alk, $SC_{1-5}$alk, $C_{1-6}$haloalk, $OC_{1-5}$haloalk, aryl and heteroaryl, or $R^4$ and $R^5$ together with the carbon atom to which they are attached form C=O.

2. A compound according to claim 1, wherein L is —N(R$^a$)C(=O)—.

3. A compound according to claim 1, wherein L is —C(=O)N(R$^a$)—.

4. A compound according to claim 1, wherein —Y—X is

5. A compound having the formula or a pharmaceutically-acceptable salt thereof, wherein:
- A is phenyl substituted with 0, 1, 2 or 3 substituents selected from F, Cl, Br, $OC_{1-4}$alk, $C_{1-4}$alk, and $C_{1-4}$haloalk;
- B is phenyl substituted with 0, 1, 2 or 3 substituents selected from F, Cl, Br, $OC_{1-4}$alk, $C_{1-4}$alk, and $C_{1-4}$haloalk;
- L is —N(R$^a$)C(=O)— or —C(=O)N(R$^a$)—;
- n is 0, 1, 2 or 3;
- $R^a$ is, independently in each instance, H or $C_{1-6}$alk;
- $R^1$ is selected from $C_{1-6}$alk, $OC_{1-5}$alk, N(R$^a$)$C_{1-5}$alk, N($C_{1-5}$ alk)$C_{1-5}$alk, aryl and heteroaryl;
- $Z^2$ is selected from O, NR$^3$, S, S(=O), S(=O)$_2$, (CR$^4$R$^5$)$_n$, C=O, C=S, C=N—R$^3$, and a direct bond;
- $R^3$ is selected from hydrogen, OH, SO$_2$, C=O, C=S, C=NH, $C_{1-6}$alk, $OC_{1-5}$alk, $SC_{1-5}$alk, $C_{1-6}$haloalk, $OC_{1-5}$ haloalk, aryl and heteroaryl; or when $Z^2$ is a direct bond, $R^3$ is a $C_3$-$C_6$ ring optionally containing a heteroatom; and
- $R^4$ and $R^5$ are independently selected from hydrogen, halogen, OH, cyano, $C_{1-6}$alk, $OC_{1-5}$alk, $SC_{1-5}$alk, $C_{1-5}$haloalk, $OC_{1-5}$haloalk, aryl and heteroaryl, or $R^4$ and $R^5$ together with the carbon atom to which they are attached form C=O.

6. A compound selected from
1-(4-(4-benzylbenzamido)-3-fluorobenzyl)azetidine-3-carboxylic acid;
1-(4-((4-benzylphenyl)carbamoyl)-3-fluorobenzyl)azetidine-3-carboxylic acid; and
1-(4-(2-(5-benzyl-2-(methylamino)phenyl)ethynyl)-3-fluorobenzyl)azetidine-3-carboxylic acid.

7. A pharmaceutical composition comprising a compound according to claim 1 and a pharmaceutically-acceptable carrier or diluent.

8. A method of treating a condition selected from transplant rejection related to solid organ transplant and islet cells; transplant rejection related to tissue; rheumatoid arthritis; lupus; insulin dependent diabetes; non-insulin dependent diabetes; multiple sclerosis; psoriasis; ulcerative colitis; inflammatory bowel disease; Crohn's disease; and acute and chronic lymphocytic leukemias and lymphomas, wherein treating is lessening or reducing the symptoms of the condition, comprising administering to a patient in need thereof a compound according to claim 1 in an amount effective to treat the condition.

* * * * *